(12) United States Patent
Nishimizu et al.

(10) Patent No.: US 9,222,915 B2
(45) Date of Patent: Dec. 29, 2015

(54) EDDY CURRENT FLAW DETECTION SYSTEM AND EDDY CURRENT FLAW DETECTION METHOD

(71) Applicant: Hitachi-GE Nuclear Energy, Ltd., Hitachi-shi, Ibaraki (JP)

(72) Inventors: Akira Nishimizu, Tokai (JP); So Kitazawa, Mito (JP); Naoyuki Kono, Mito (JP); Hisashi Endo, Hitachi (JP); Kenichi Otani, Hitachi (JP); Taiichiro Yamada, Hitachi (JP); Hirofumi Ouchi, Mito (JP); Isao Yoshida, Iwaki (JP); Yoshio Nonaka, Mito (JP); Masafumi Imai, Hitachiota (JP)

(73) Assignee: Hitachi-GE Nuclear Energy, Ltd., Hitachi-shi (JP)

( * ) Notice: Subject to any disclaimer, the term of this patent is extended or adjusted under 35 U.S.C. 154(b) by 450 days.

(21) Appl. No.: 13/748,165

(22) Filed: Jan. 23, 2013

(65) Prior Publication Data
US 2013/0193960 A1 Aug. 1, 2013

(30) Foreign Application Priority Data

Jan. 27, 2012 (JP) ................................. 2012-015774

(51) Int. Cl.
*G01N 27/82* (2006.01)
*G01N 27/90* (2006.01)

(52) U.S. Cl.
CPC ............ *G01N 27/9006* (2013.01); *G01N 27/82* (2013.01); *G01N 27/902* (2013.01)

(58) Field of Classification Search
CPC .......... G01B 7/004; G01B 7/00; G01B 5/008; G01N 27/9046; G01N 27/902; G01N 27/82; G01N 27/9013; G01N 27/904; G01N 27/9006; G01N 27/9073; G01N 27/72; G01N 2291/02854; G01N 2291/048; G01N 2291/105; G01N 2291/106; G01N 29/365; G01N 29/0618; G01N 29/0645; G01N 29/226; G06T 7/0002; H01F 5/00; G01M 5/0033; G01R 33/10; G01R 15/142; Y10S 128/916

USPC ......... 324/216, 217, 222, 228–243, 456, 718; 702/35–38, 150–153
See application file for complete search history.

(56) References Cited

U.S. PATENT DOCUMENTS

| 4,855,677 A * | 8/1989 | Clark, Jr. ........... G01N 27/9046 324/220 |
| 4,856,337 A * | 8/1989 | Metala ................ G01N 27/902 324/220 |

(Continued)

FOREIGN PATENT DOCUMENTS

| JP | 2-302663 A | 12/1990 |
| JP | 2006-329632 A | 12/2006 |

(Continued)

OTHER PUBLICATIONS

Nelligan et al., Introduction to Eddy Current Testing, Jun. 4, 2015 (No Way Back Date), Olympus Inc. pp. 1-6.*

(Continued)

*Primary Examiner* — Patrick Assouad
*Assistant Examiner* — Sean Curtis
(74) *Attorney, Agent, or Firm* — Crowell & Moring LLP

(57) ABSTRACT

An eddy current flaw detection system includes an eddy current flaw detection probe having a substrate facing an inspection surface, and at least one exciting coil and at least two detecting coils provided on the substrate, a scanning device which scans the probe on the inspection surface, a scan control device which drives and controls the scanning device, an eddy current flaw detection device which acquires results of detection of a plurality of detection points corresponding to combinations of the exciting and detecting coils for each scan position of the probe, and a data processing/display device which processes data from the scan control device and the eddy current flaw detection device and thereby displays a result of flaw detection. The data processing/display device acquires three-dimensional coordinates of the detection points for each scan position of the probe and thereby creates three-dimensional flaw detection data.

8 Claims, 16 Drawing Sheets

(56) References Cited

U.S. PATENT DOCUMENTS

| | | | | |
|---|---|---|---|---|
| 4,955,235 | A * | 9/1990 | Metala | G01N 27/902 324/226 |
| 5,130,652 | A * | 7/1992 | Kawakami | G01N 27/902 324/238 |
| 5,161,413 | A * | 11/1992 | Junker | G01N 29/223 73/634 |
| 5,334,934 | A * | 8/1994 | Viertl | G01N 27/902 324/220 |
| 5,430,376 | A * | 7/1995 | Viertl | B82Y 15/00 324/226 |
| 5,510,709 | A * | 4/1996 | Hurley | G01N 27/9013 324/225 |
| 5,623,203 | A * | 4/1997 | Hosohara | G01N 27/902 324/220 |
| 5,648,721 | A * | 7/1997 | Wincheski | G01N 27/9033 324/209 |
| 5,710,378 | A * | 1/1998 | Dykes | G01N 27/902 324/262 |
| 5,895,439 | A * | 4/1999 | Fisher | G06T 11/206 702/36 |
| 6,037,768 | A * | 3/2000 | Moulder | G01N 27/9046 324/202 |
| 6,150,809 | A * | 11/2000 | Tiernan | G01N 27/82 324/225 |
| 6,344,741 | B1 * | 2/2002 | Giguere | G01N 27/9046 324/225 |
| 6,370,485 | B1 * | 4/2002 | Kawata | G01N 27/9046 702/113 |
| 6,456,066 | B1 * | 9/2002 | Burd | G01N 27/902 324/220 |
| 6,501,267 | B1 * | 12/2002 | Kurokawa | G01N 27/904 324/242 |
| 6,504,363 | B1 * | 1/2003 | Dogaru | G01N 27/9006 324/235 |
| 6,636,037 | B1 * | 10/2003 | Ou-Yang | G01N 27/902 324/232 |
| 6,670,808 | B2 * | 12/2003 | Nath | G01N 27/904 324/202 |
| 6,762,604 | B2 * | 7/2004 | Le | G01B 7/105 324/230 |
| 6,777,931 | B1 * | 8/2004 | Takada | G01N 29/0609 324/226 |
| 6,820,032 | B2 * | 11/2004 | Wenzel | G01B 11/2518 702/167 |
| 6,836,735 | B2 * | 12/2004 | Burkhardt | G09B 19/00 702/35 |
| 6,888,346 | B2 * | 5/2005 | Wincheski | G01N 27/9033 324/235 |
| 6,911,826 | B2 * | 6/2005 | Plotnikov | G01N 27/904 324/238 |
| 6,914,427 | B2 * | 7/2005 | Gifford | G01N 27/904 324/240 |
| 7,034,831 | B2 * | 4/2006 | Wenzel | G05B 19/00 345/442 |
| 7,233,867 | B2 * | 6/2007 | Pisupati | G01N 27/9046 324/255 |
| 7,235,967 | B2 * | 6/2007 | Nishimizu | G01N 27/9013 324/238 |
| 7,272,254 | B2 * | 9/2007 | Shankarappa | G06K 9/00 382/149 |
| 7,288,941 | B2 * | 10/2007 | Redko | C01B 31/04 324/222 |
| 7,358,721 | B2 * | 4/2008 | Narishige | G01N 27/902 324/240 |
| 7,375,514 | B2 * | 5/2008 | Rempt | G01N 27/904 324/235 |
| 7,385,392 | B2 * | 6/2008 | Schlicker | G01N 27/82 324/242 |
| 7,508,201 | B2 * | 3/2009 | Tada | G01B 7/105 324/229 |
| 7,508,971 | B2 * | 3/2009 | Vaccaro | G01B 5/008 382/141 |
| 7,560,920 | B1 * | 7/2009 | Ouyang | G01N 27/902 324/240 |
| 7,626,383 | B1 * | 12/2009 | Sun | G01N 27/82 324/232 |
| 7,772,840 | B2 * | 8/2010 | Suzuki | G01N 27/902 324/238 |
| 7,817,845 | B2 * | 10/2010 | Suh | G01N 27/902 324/137 |
| 7,830,140 | B2 * | 11/2010 | Tralshawala | G01R 33/10 324/202 |
| 7,872,472 | B2 * | 1/2011 | Suzuki | G01N 27/902 324/238 |
| 7,911,206 | B2 * | 3/2011 | Nishimizu | G01N 27/9046 324/228 |
| 8,013,600 | B1 * | 9/2011 | Yepez, III | G01N 27/9033 324/240 |
| 8,183,862 | B2 * | 5/2012 | Endo | G01N 27/9046 324/232 |
| 8,228,058 | B2 * | 7/2012 | Nishimizu | G01N 27/9033 324/222 |
| 2005/0007108 | A1 * | 1/2005 | Dogaru | G01N 27/904 324/235 |
| 2009/0102473 | A1 * | 4/2009 | Narishige | G01N 27/90 324/240 |
| 2009/0230952 | A1 * | 9/2009 | Endo | G01N 27/9046 324/238 |
| 2010/0079157 | A1 * | 4/2010 | Wincheski | G01N 27/904 324/699 |
| 2010/0295545 | A1 * | 11/2010 | Holzl | G01N 27/9026 324/241 |
| 2012/0025816 | A1 * | 2/2012 | Lepage | G01N 27/904 324/240 |
| 2012/0062728 | A1 * | 3/2012 | Oikawa | G01N 21/954 348/128 |
| 2013/0241541 | A1 * | 9/2013 | Endo | G01N 27/87 324/232 |
| 2014/0184215 | A1 * | 7/2014 | Nishimizu | G01N 27/902 324/256 |

FOREIGN PATENT DOCUMENTS

| | | |
|---|---|---|
| JP | 2008-8806 A | 1/2008 |
| JP | 2008-298478 A | 12/2008 |
| JP | 2009-19909 A | 1/2009 |

OTHER PUBLICATIONS

Uesaka et al., Eddy-Current Testing by Flexible Microloop Magnetic Sensor Array, IEEE Transactions of Magnetics, vol. 34, No. 4, Jul. 1998, pp. 1-11.*

Chady et al., Crack Detection and Recognition Using Eddy Current Differential Probe, IEEE Transactions on Magnetics, vol. 35, No. 3, May 1999, pp. 1-4.*

Brauer et al., Defect Detection in Conducting Materials Using Eddy Current Testing Techniques, Serbian Journal of Electrical Engineering, vol. 11, No. 4, Dec. 2014, pp. 1-15.*

He-yun et al., Application of "Zoom-In" Technique in 3D Remote Field Eddy Current Effect Computation, IEEE Transactions on Magnetics, vol. 26, No. 2, Mar. 1990, pp. 1-4.*

Bisiaux et al., Simulation of 3D Eddy Current Testing of Tubes with External Probes: Modelling Approach and Experimental Validations, ECNDT 2006—We.2.3.1, Jan. 2007, pp. 1-8.*

Grimberg et al., 3-D Eddy Current Nondestructive Testing Modeling for Surface Flaws, IRSID, Dept of Electrotechnique, Date Unknown, pp. 1-7.*

* cited by examiner

| SCAN POSITION OF PROBE (NUMBER OF START TRIGGER SIGNALS) CHANNEL | FIRST | SECOND | ・・・ | LAST |
|---|---|---|---|---|
| 1ch | ×× | ×× | | ×× |
| 2ch | ×× | ×× | | ×× |
| ⋮ | | | | |
| Nch | ×× | ×× | | ×× |
| ⋮ | | | | |
| LAST ch | ×× | ×× | | ×× |

EDDY CURRENT FLAW DETECTION SYSTEM AND EDDY CURRENT FLAW DETECTION METHOD

BACKGROUND OF THE INVENTION

1. Field of the Invention

The present invention relates to an eddy current flaw detection system and an eddy current flaw detection method for scanning an eddy current flaw detection probe on an inspection surface.

2. Description of the Related Art

An eddy current flaw detection method is an inspection method of causing an alternating magnetic field generated by an exciting coil to induce eddy currents in a surface layer portion of a conductive object to be inspected and detecting a disturbance in eddy currents due to a flaw or crack as a change (change in output voltage) in impedance of a detecting or sensing coil, thereby determining the presence or absence of the flaw.

There has recently been proposed an eddy current flaw detection system using an eddy current flaw detection probe (hereinafter called a "multi-coil probe") having a plurality of coils arranged on a substrate for the purpose of speeding up inspections (refer to, for example, JP-2008-8806-A (refer to FIGS. 14 and 15, etc.)). In the eddy current flaw detection system described in JP-2008-8806-A, a plurality of coils arranged in a direction orthogonal to a scanning direction of a multi-coil probe are sequentially switched to exciting and detecting coils while the multi-coil probe is being scanned on an inspection surface. That is, the multi-coil probe has a plurality of combinations (channels) of the exciting and detecting coils. Thus, for example, as compared with a case in which an eddy current flaw detection probe having only a single combination of exciting and detecting coils is used, a wide range of scanning is enabled and the shortening of an inspection time is made possible. Further, since the substrate of the multi-coil probe has flexibility (ductility), the multi-coil probe is capable of following the shape of the inspection surface.

In the above-described eddy current flaw detection system, each scan position of the probe is recorded and a result of detection of each channel (output voltage of detecting coil) is recorded. When a flat inspection surface is flaw-detected, for example, a scan area is displayed by a two-dimensional coordinate system in which each scan position of the probe and each channel position (in other words, the position on the substrate, of a detection point corresponding to each combination of exciting and detecting coils, and in JP-2008-8806-A, the position in the direction orthogonal to the probe scanning direction) on the substrate are taken as coordinates. Results of detection of the respective channels are also displayed in color tones of pixels of their corresponding coordinates. With such a display of flaw detection results, it is possible to determine the presence or absence of a flaw and evaluate the position and length of the flaw.

Incidentally, objects to be inspected by the eddy current flaw detection system have been expanded up to those each having an inspection surface of a complicate three-dimensional shape, like, for example, a weld between a reactor pressure vessel (RPV) and a stub tube of a control Rod Drive (CRD) (refer to, for example, JP-2008-298478-A (refer to FIGS. 20 and 21, etc.)).

SUMMARY OF THE INVENTION

Although not described in JP-2008-298478-A, even when an inspection surface having a complicate three-dimensional shape is flaw-detected using a multi-coil probe, it is better to display a result of flaw detection for the purpose of determining the presence or absence of a flaw and evaluating the position and length of the flaw. Thus, as with the related art described in JP-2008-8806-A, there is considered, for example, a method of displaying a scan area by a two-dimensional coordinate system in which each probe scan position and each channel position on a substrate are taken as coordinates, and displaying detection results of respective channels in color tones of pixels of their corresponding coordinates.

For example, however, the surface (inspection surface) of the above-described weld between the reactor pressure vessel and the stub tube of the control rod drive is approximately in the form of a truncated conical side surface in its entirety and takes on such a complicate three-dimensional shape that its axial section is concave and its curvature changes depending on a circumferential position. Therefore, when the multi-coil probe is scanned in the circumferential direction of the inspection surface while the multi-coil probe is being brought into close contact with such an inspection surface, a portion on the one side of the probe and a portion on the other side thereof as viewed in the direction intersecting the direction of scanning of the probe are different in terms of the length of a scan trajectory, combined with deformation of the substrate. As the case may be, there is a need to change the attitude angle of the multi-coil probe according to the scan position of the probe in order to bring the probe into close contact with the inspection surface. Thus, when the scan area is represented by the above-described two-dimensional coordinate system, distortion occurs and a result of flaw detection cannot accurately be displayed. As a result, it is not possible to evaluate the position and length of a flaw accurately.

An object of the present invention is to provide an eddy current flaw detection system and an eddy current flaw detection method capable of enhancing the accuracy of display of a result of flaw detection and improving the accuracy of evaluation of a flaw.

(1) In order to achieve the above object, the present invention provides an eddy current flaw detection system including: an eddy current flaw detection probe having a substrate facing an inspection surface, and at least one exciting coil and at least two detecting coils provided on the substrate; a scanning device which scans the eddy current flaw detection probe on the inspection surface; a scan control device which drives and controls the scanning device to control a scan position and an attitude angle of the eddy current flaw detection probe; and an eddy current flaw detection device which acquires results of detection of a plurality of detection points corresponding to combinations of the exciting and detecting coils for each scan position of the eddy current flaw detection probe, wherein the eddy current flaw detection system includes: detection point three-dimensional coordinate acquiring means which acquires three-dimensional coordinates of the detection points for each scan position of the eddy current flaw detection probe; three-dimensional flaw detection data generating means which generates three-dimensional flaw detection data including the three-dimensional coordinates of the detection points and detection results thereof corresponding to the three-dimensional coordinates; and display means which displays a three-dimensional model of the inspection surface and displays the detection results of the detection points on the three-dimensional model of the inspection surface in color tones, based on the three-dimensional flaw detection data.

The present invention is suitable for, for example, a case where a portion on the one side of an eddy current flaw detection probe and a portion on the other side thereof as viewed in the direction intersecting the direction of scanning of the probe are different in terms of the length of a scan trajectory as in the case where the probe is scanned over a surface (inspection surface) of a weld between a reactor pressure vessel and a stub tube of a control rod drive. In order to cope with such a case, in the present invention, three-dimensional coordinates of a plurality of detection points corresponding to combinations (channels) of exciting and detecting coils are acquired for each scan position of the eddy current flaw detection probe. Then, three-dimensional flaw detection data including the three-dimensional coordinates of the detection points and results of detection thereof corresponding to those are created or generated. Further, a three-dimensional model of the inspection surface is displayed, and the results of detection of the detection points are represented in color tones on the three-dimensional model of the inspection surface, based on the three-dimensional flaw detection data. Thus, as compared with the case where as described in JP-2008-8806-A, for example, the scan area is represented by the two-dimensional coordinate system in which each probe scan position and each channel position on the substrate are taken as the coordinates, and detection results of respective channels are represented in color tones of pixels of their corresponding coordinates, no distortion occurs and the accuracy of display of a flaw detection result can be enhanced. As a result, the accuracy of evaluation of the position and length and the like of a flaw can be improved.

(2) In the above (1), preferably, the eddy current flaw detection system further includes a probe structure storing means which stores in advance relations in position between the detection points on the substrate of the eddy current flaw detection probe, wherein the detection point three-dimensional coordinate acquiring means includes: first detection point three-dimensional coordinate computing means which computes a three-dimensional coordinate of a specific detection point of the detection points corresponding to the scan position of the eddy current flaw detection probe based on control parameters of the scanning device, probe attitude angle computing means which computes a yaw angle of the eddy current flaw detection probe based on the control parameters of the scanning device, and second detection point three-dimensional coordinate computing means which plots the specific detection point on the three-dimensional model of the inspection surface, plots other detection points than the specific detection point on the three-dimensional model of the inspection surface based on the yaw angle of the eddy current flaw detection probe and the relations in position between the detection points on the substrate, and thereby computes three-dimensional coordinates of the other detection points.

(3) In the above (2), preferably, the detection point three-dimensional coordinate acquiring means further includes probe pressing direction computing means which computes a direction for pressing the eddy current flaw detection probe against the inspection surface based on the control parameters of the scanning device, and wherein when the computed three-dimensional coordinate of the specific detection point does not coincide with the three-dimensional model of the inspection surface, the first detection point three-dimensional coordinate computing means moves the three-dimensional coordinate of the specific detection point in the pressing direction to correct the three-dimensional coordinate so as to coincide with the three-dimensional model of the inspection surface.

(4) In the above (1), preferably, the eddy current flaw detection system further includes a plurality of markers provided in the substrate of the eddy current flaw detection probe; imaging means which images the markers for each scan position of the eddy current flaw detection probe; and probe structure storing means which stores in advance layout relations between the substrate and the markers at the eddy current flaw detection probe and layout relations between the substrate and the detection points, wherein the detection point three-dimensional coordinate acquiring means includes: marker three-dimensional coordinate computing means which computes three-dimensional coordinates of the markers based on images of the markers for each scan position of the eddy current flaw detection probe, and detection point three-dimensional coordinate computing means which computes a shape and layout of the substrate based on the three-dimensional coordinates of the markers and the layout relations between the substrate and the markers for each scan position of the eddy current flaw detection probe, and further computes three-dimensional coordinates of the detection points based on the layout relations between the substrate and the detection points.

(5) In the above (4), preferably, the eddy current flaw detection system further includes three-dimensional model generating means which generates a three-dimensional model of the inspection surface based on the three-dimensional coordinates of the detection points or the three-dimensional coordinates of the markers which have been computed for each scan position of the eddy current flaw detection probe, wherein the display means displays the three-dimensional model of the inspection surface generated by the three-dimensional model generating means.

(6) In order to achieve the above object, the present invention provides an eddy current flaw detection method including the steps of: scanning an eddy current flaw detection probe on an inspection surface, the eddy current flaw detection probe having a substrate facing the inspection surface, and at least one exciting coil and at least two detecting coils provided on the substrate; and acquiring results of detection of a plurality of detection points corresponding to combinations of the exciting and detecting coils for each scan position of the eddy current flaw detection probe, wherein the eddy current flaw detection method includes: a first procedure for acquiring three-dimensional coordinates of the detection points for each scan position of the eddy current flaw detection probe; a second procedure for generating three-dimensional flaw detection data including the three-dimensional coordinates of the detection points and detection results thereof corresponding to the three-dimensional coordinates; and a third procedure for displaying a three-dimensional model of the inspection surface and displaying the detection results of the detection points on the three-dimensional model of the inspection surface in color tones based on the three-dimensional flaw detection data.

(7) In the above (6), preferably, the first procedure includes a fourth procedure for computing a three-dimensional coordinate of a specific detection point of the detection points corresponding to the scan position of the eddy current flaw detection probe based on control parameters of a scanning device for scanning the eddy current flaw detection probe; a fifth procedure for computing a yaw angle of the eddy current flaw detection probe based on the control parameters of the scanning device; and a sixth procedure for plotting the specific detection point on the three-dimensional model of the inspection surface, plotting other detection points than the specific detection point on the three-dimensional model of the inspection surface based on the yaw angle of the eddy current flaw detection probe and relations in position between the detection points on the substrate, and thereby computing three-dimensional coordinates of the other detection points.

(8) In the above (7), preferably, the first procedure further includes a seventh procedure for computing a direction for pressing the eddy current flaw detection probe against the inspection surface based on the control parameters of the scanning device, wherein when the computed three-dimensional coordinate of the specific detection point does not coincide with the three-dimensional model of the inspection surface, the fourth procedure moves the three-dimensional coordinate of the specific detection point in the pressing direction to correct the three-dimensional coordinate so as to coincide with the three-dimensional model of the inspection surface.

(9) In the above (6), preferably, the first procedure includes: an eighth procedure for imaging a plurality of markers provided in the substrate of the eddy current flaw detection probe for each scan position of the eddy current flaw detection probe; a ninth procedure for computing three-dimensional coordinates of the markers based on images of the markers for each scan position of the eddy current flaw detection probe; and a tenth procedure for computing a shape and layout of the substrate based on the three-dimensional coordinates of the markers and layout relations between the substrate and the markers for each scan position of the eddy current flaw detection probe, and further computing three-dimensional coordinates of the detection points based on layout relations between the substrate and the detection points.

(10) In the above (9), preferably, the eddy current flaw detection method further includes an eleventh procedure for generating a three-dimensional model of the inspection surface based on the three-dimensional coordinates of the detection points or the three-dimensional coordinates of the markers which have been computed for each scan position of the eddy current flaw detection probe, wherein the third procedure displays the three-dimensional model of the inspection surface generated in the eleventh procedure.

According to the present invention, the accuracy of display of a result of flaw detection can be enhanced, and the accuracy of evaluation of a flaw can be improved.

BRIEF DESCRIPTION OF DRAWINGS

These and other features, objects and advantages of the present invention will become more apparent from the following description when taken in conjunction with the accompanying drawings wherein.

DESCRIPTION OF THE PREFERRED EMBODIMENTS

A first embodiment of the present invention will be described with reference to the accompanying drawings. The present embodiment will be described by taking for example a case where a weld between a reactor pressure vessel and a stub tube of a control rod drive is inspected.

Figure 1:
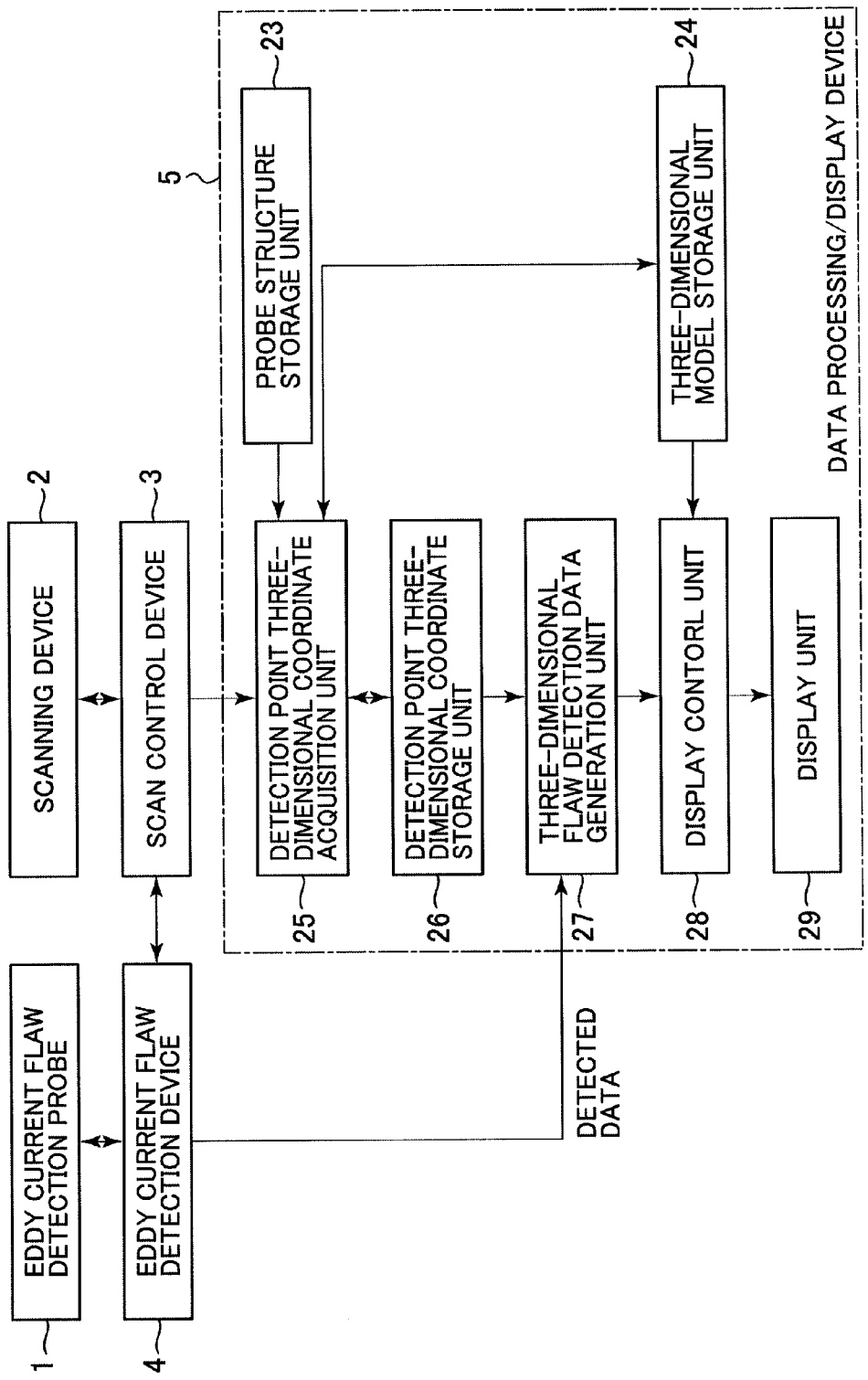
FIG. 1 is a block diagram showing a configuration of an eddy current flaw detection system according to a first embodiment of the present invention.
Figure 2A:
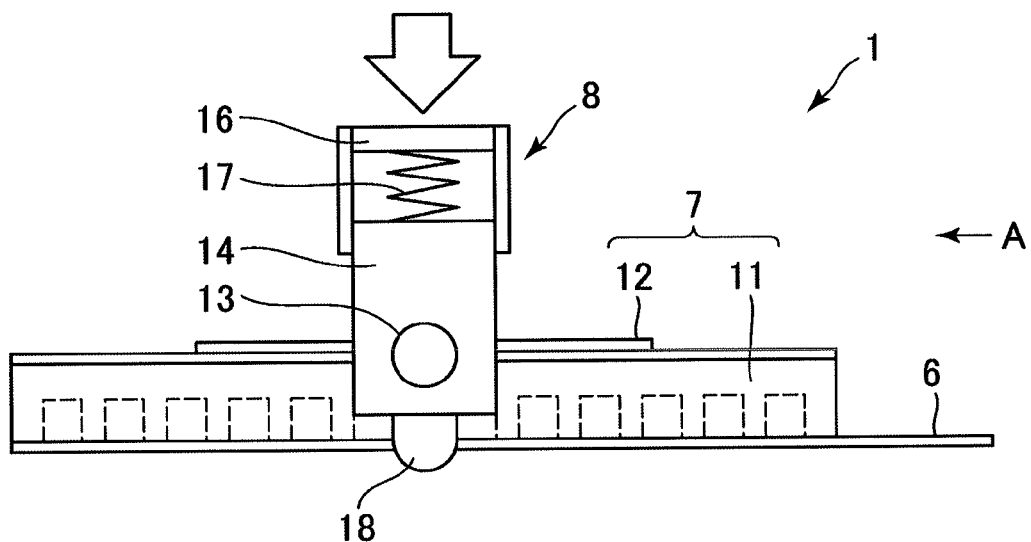
FIGS. 2A and 2B are side views illustrating an overall structure of an eddy current flaw detection probe in the first embodiment of the present invention.
Figure 2B:
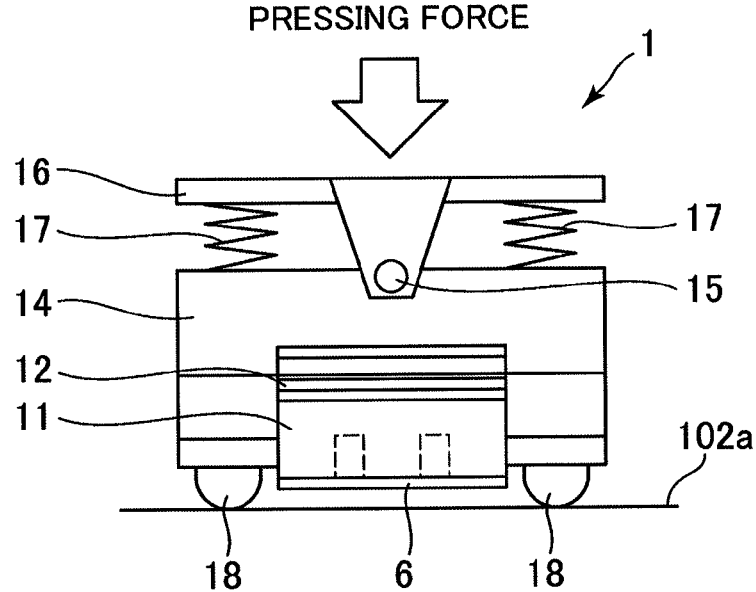
Figure 3:
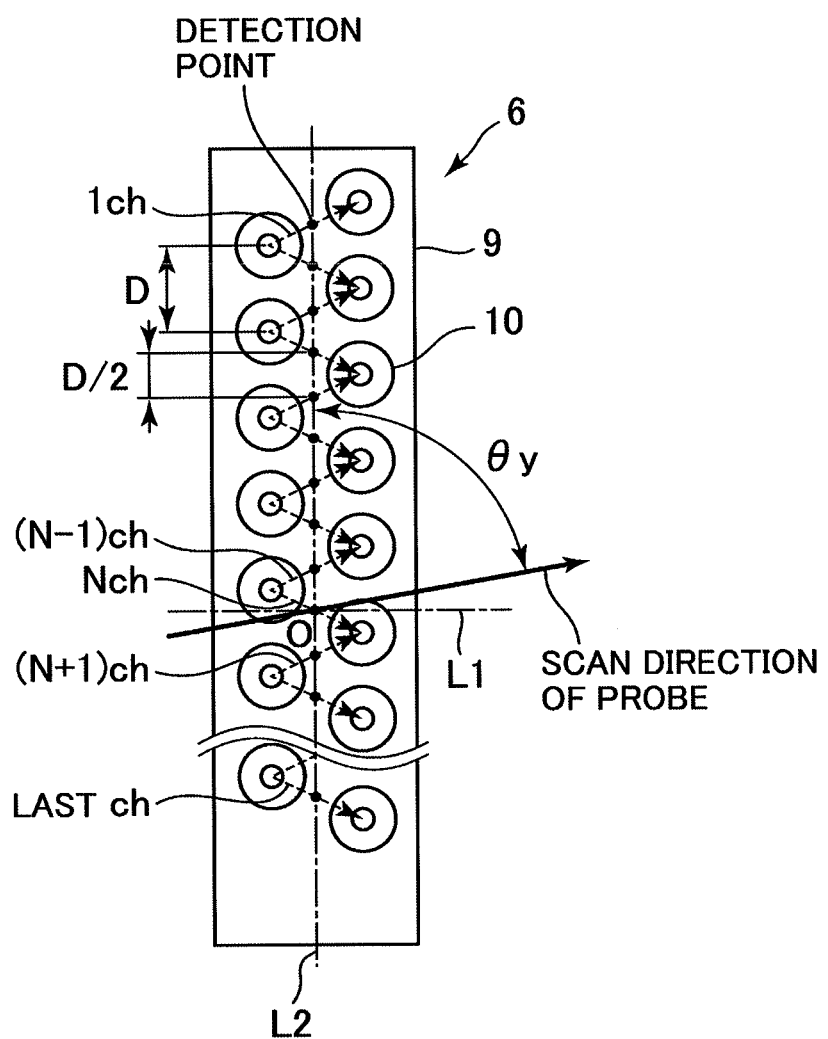
FIG. 3 is a plan view showing a structure of a sensor part of the eddy current flaw detection probe in the first embodiment of the present invention and also shows combined patterns of exciting and detecting coils.
Figure 4A:
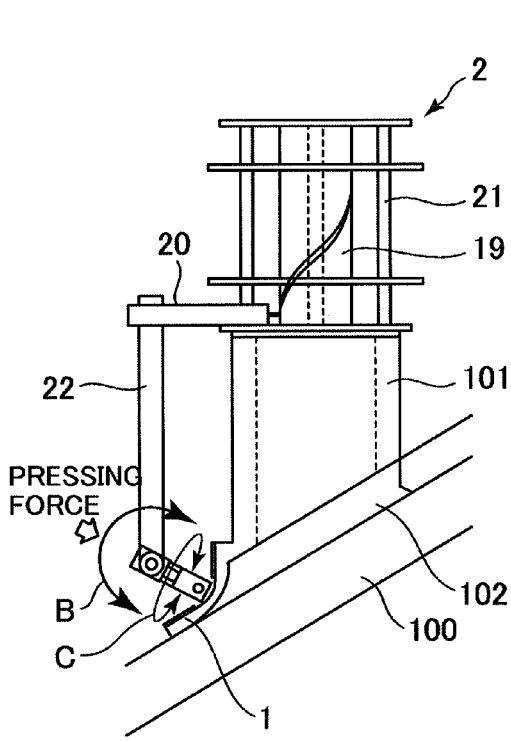
FIGS. 4A and 4B are each side views illustrating a structure of a scanning device in the first embodiment of the present invention along with the eddy current flaw detection probe and an object to be inspected.
Figure 4B:
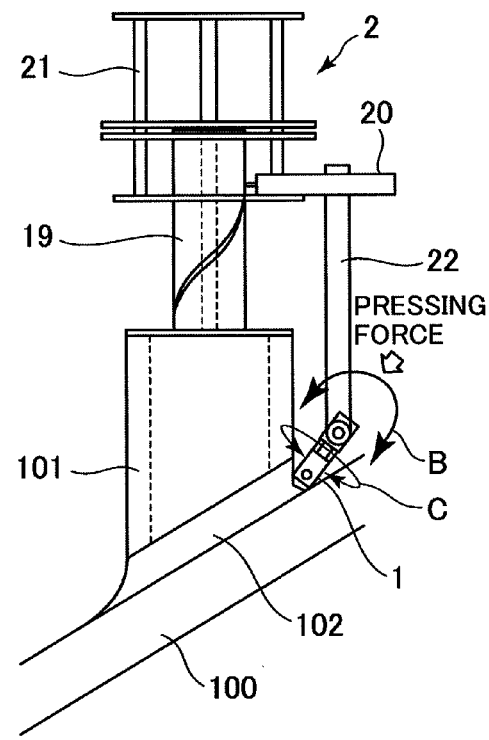
Figures 5, 6:
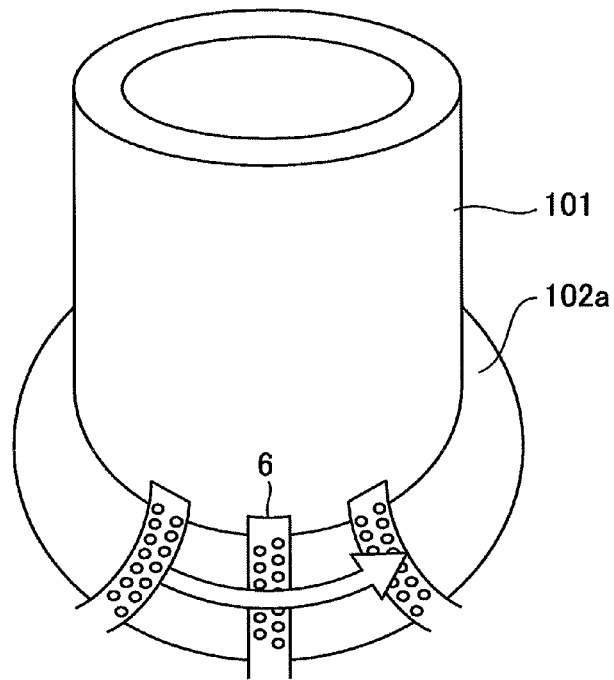
FIG. 5 is a perspective view for describing the scanning of the eddy current flaw detection probe in the first embodiment of the present invention.
FIG. 6 is a diagram depicting detected data of an eddy current flaw detection device in the first embodiment of the present invention.

FIG. 1 is a block diagram showing a configuration of an eddy current flaw detection system according to the present embodiment. FIG. 2A is a side view illustrating an overall structure of an eddy current flaw detection probe in the present embodiment. FIG. 2B is a side view as viewed from a direction indicated by arrow A in FIG. 2A. FIG. 3 is a plan view showing a structure of a sensor part of the eddy current flaw detection probe in the present embodiment. FIGS. 4A and 4B are side views showing a structure of a scanning device in the present embodiment. FIG. 5 is a perspective view for describing the scanning of the eddy current flaw detection probe in the present embodiment.

The eddy current flaw detection system according to the present embodiment is equipped with an eddy current flaw detection probe (hereinafter called a multi-coil probe) 1 disposed on a surface (inspection surface) 102*a* of a weld 102 between a reactor pressure vessel 100 and a stub tube 101 of a control rod drive, a scanning device 2 which scans the multi-coil probe 1 on the inspection surface 102*a*, a scan control device 3 which drives and controls the scanning device 2 to control a scan position and an attitude angle of the multi-coil probe 1, an eddy current flaw detection device 4 which performs flaw detection control of the multi-coil probe 1, and a data processing/display device 5 which processes data from the scanning device 3 and eddy current flaw detection device 4 and thereby displays a result of flaw detection.

The multi-coil probe 1 is equipped with a sensor part 6, an elastic part 7 for bringing the sensor part 6 into close contact with the inspection surface 102a, and a sensor support part 8 which supports the sensor part 6 through the elastic part 7. The sensor part 6 has a flexible (ductile) substrate 9 which faces the inspection surface 102a, and a plurality of coils 10 fixed to the upper side (side opposite to the inspection surface 102a) of the substrate 9 and arranged in a triangular lattice form in two rows, for example. The sensor part 6 is capable of following the shape of the inspection surface.

The elastic part 7 is composed of a sponge (porous elastic body) 11 which is bonded to the upper side of the substrate 9 and accommodates the coils 10 therein, and a laminated leaf spring 12 bonded to the upper side of the sponge 11. The laminated leaf spring 12 is made up of a plurality of leaf springs laminated on each other in such a manner that the thickness (in other words, the modulus of elasticity) of a central portion thereof as viewed in the longitudinal direction (horizontal direction in FIG. 2A) of the sensor part 6 becomes large and the thickness (in other words, the modulus of elasticity) thereof on both end sides thereof as viewed in its longitudinal direction becomes small. Thus, even if the sectional curvature of the inspection surface 102a changes, the whole surface of the sensor part 6 can be pressed. Accordingly, the whole surface of the sensor part 6 is brought into close contact with the inspection surface 102a. Incidentally, only one leaf spring may be used instead of the laminated leaf spring 12.

The sensor support part 8 is composed of an approximately inverted U-shaped support table 14 which supports the elastic part 7 and the sensor part 6 through a pin 13 that extends in the transverse direction (horizontal direction in FIG. 2B) of the sensor part 6, a base 16 which tiltably supports the support table 14 through a shaft 15 that extends in the longitudinal direction of the sensor part 6, and a pair of springs 17 provided between the support table 14 and the base 16. The shaft 15, base 16 and pair of springs 17 configure a so-called gimbal, which tilts the sensor part 6 so as to follow the tilt of the inspective surface 102a and thereby improves adhesion between the sensor part 6 and the inspection surface 102a. Incidentally, a pair of ground detectors 18 may be provided at their corresponding ends of the support table 14 to confirm adhesion between the sensor part 6 and the inspection surface 102a, based on the results of their detection. Alternatively, a pair of ground members (e.g., hemispheric members) may be provided at their corresponding ends of the support table 14.

The scanning device 2 is equipped with a body part 19 provided so as to be nearly concentric with the stub tube 101 of the control rod drive, a rotation/up-and-down movement mechanism 21 which rotates an arm 20 about the body part 19 in its circumferential direction and vertically moves the arm 20, and a slide mechanism (not shown) which slides a manipulator 22 along the longitudinal direction (in other words, the radial direction of the stub tube 101) of the arm 20. The base 16 of the multi-coil probe 1 described above is mounted to the tip side (lower side in FIGS. 4A and 4B) of the manipulator 22.

Although not illustrated in detail, the manipulator 22 has a rotation mechanism which is rotated in the direction indicated by arrow B in FIGS. 4A and 4B to enable a roll angle θr and the like of the sensor part 6 of the multi-coil probe 1 to be adjusted, a rotation mechanism which is rotated in the direction indicated by arrow C in FIGS. 4A and 4B to enable a pitch angle θp and the like of the sensor part 6 of the multi-coil probe 1 to be adjusted, and a rotation mechanism which is rotated about its vertical axis to enable a yaw angle θy (in other words, an angle as viewed in the longitudinal direction of the probe 1 relative to the direction of scanning of the probe 1 as shown in FIG. 3) and the like of the sensor part 6 of the multi-coil probe 1 to be adjusted.

Here, the surface (inspection surface 102a) of the weld 102 is approximately in the form of a truncated conical side surface in its entirety and takes on such a complicate three-dimensional shape that its axial section is concave and its curvature changes depending on a circumferential position (refer to FIGS. 4A and 4B and FIG. 5). Therefore, when the sensor part 6 of the multi-coil probe 1 is scanned in the circumferential direction of the inspection surface 102a while being brought into close contact with the inspection surface 102a, a portion on the one side of the sensor part 6 and a portion on the other side thereof as viewed in the direction (in other words, the longitudinal direction of the sensor part 6) intersecting the direction of scanning of the probe 1 are different in terms of the length of a scan trajectory, combined with deformation of the substrate 9. In some cases, in order to bring the sensor part 6 of the multi-coil probe 1 into close contact with the inspection surface 102a, there is a need to change the attitude angle of the probe 1 according to the scan position of the probe 1.

Control parameters for the rotation/up-and-down movement mechanism 21, slide mechanism and manipulator 22 have been set to and stored in the scan control device 3 in advance for each scan position of the probe 1 (specifically, for every number of start trigger signals to be described). The scan control device 3 drives and controls the rotation/up-and-down movement mechanism 21, slide mechanism and manipulator 22, based on the control parameters set and stored in advance to thereby scan the multi-coil probe 1 in the circumferential direction of the inspection surface 102a (in other words, along a weld line). At this time, the scan position and the attitude angle (specifically, the above roll angle θr, pitch angle θp and yaw angle θy) of the multi-coil probe 1 are controlled, while a pressing force for pressing the multi-coil probe 1 against the inspection surface 102a is applied thereto from the manipulator 22 (refer to FIGS. 4A and 4B) and thereby making the multi-coil probe 1 adhere tightly to the inspection surface 102a.

The scan control device 3 transmits the start trigger signal to the eddy current flaw detection device 4 each time the scan control device 3 drives and controls the scanning device 2 to scan the multi-coil probe 1 in a predetermined scan pitch (in other words, for each scan position of the multi-coil probe 1).

When the eddy current flaw detection device 4 receives the start trigger signal from the scan control device 3, the eddy current flaw detection device 4 sequentially switches the coils 10 to the combinations (1 channel, 2 channel, . . . , N channel, . . . last channel) of exciting and detecting coils placed in a layout relationship as viewed in the transverse direction of the probe 1 as indicated by dotted lines in FIG. 3, for example. To be more specific, the eddy current flaw detection device 4 switches the coils 10 placed in a first row (row on the left side in FIG. 3) to their corresponding exciting coils one by one, and switches the two coils placed in a second row (row on the right side in FIG. 3) and adjacent to the exciting coils to their corresponding detecting coils. An eddy current is induced in a surface layer portion of the weld 102 by an alternative magnetic field produced by each exciting coil, thereby detecting a disturbance in eddy current due to a flaw as a change (change in output voltage) in the impedance of each detecting coil. A result of this detection is acquired as one for each detection point (specifically, an intermediate point between the exciting and detecting coils as indicated by a black circle in FIG. 3) corresponding to the combination of the exciting and detecting coils. Thus, results (output voltages of detecting coils) of detection of a plurality of detection points corresponding to a plurality of channels are acquired for each scan position of multi-coil probe 1 (specifically, for every number of trigger signals described above). Detected data (refer to FIG. 6) composed of detection results corresponding to the scan positions (specifically, the number of trigger signals described above) of the multi-coil probe 1 and the channel numbers are created and recorded.

Incidentally, as shown in FIG. 3, a specific detection point O corresponding to a specific N channel is given as the center point of the substrate 9 and equivalent to a point where an axial center L1 of the pin 13 and an axial center L2 of the shaft 15 both intersect when they are reflected on the substrate 9. Three-dimensional coordinate of the detection point O corresponds to each scan position of the probe 1 and is insensitive to the attitude angle of the probe 1.

The data processing/display device 5 that is an essential part of the present embodiment has, as functional constituents, a probe structure storage unit 23, a three-dimensional model storage unit 24, a detection point three-dimensional coordinate acquisition unit 25, a detection point three-dimensional coordinate storage unit 26, a three-dimensional flaw detection data generation unit 27, a display control unit 28 and a display unit (monitor) 29.

The probe structure storage unit 23 stores in advance, positional relations between the detection points on the substrate 9 of the multi-coil probe 1. In particular, in the present embodiment, since the detection points for the plural channels are arranged in the longitudinal direction of the probe 1 as shown in FIG. 3, coil intervals D and detection-point intervals D/2, and the like on the substrate 9 as viewed in the longitudinal direction of the probe 1 have been stored in advance.

The three-dimensional model storage unit 24 stores in advance, a three-dimensional model 30 of the surface (inspection surface) of the weld 102, and a three-dimensional model 31 of a surface of a peripheral structure (specifically, the reactor pressure vessel 100, the stub tube 101 of the control rod drive, etc.). Incidentally, the three-dimensional model is data of three-dimensional coordinates. Design data may be used, but actually-measured data may preferably be used.

Figure 7:
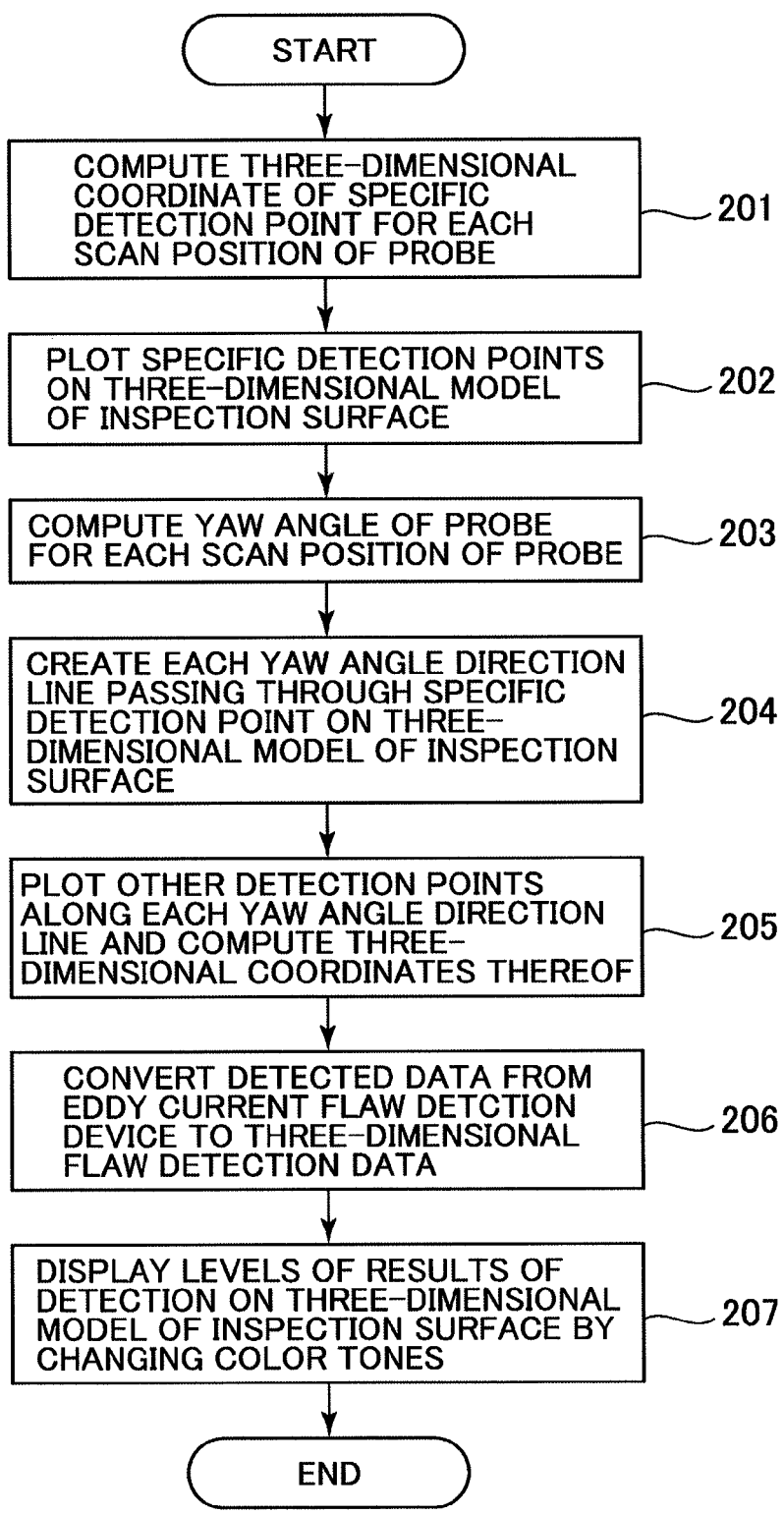
FIG. 7 is a flowchart showing the contents of control of a data processing/display device in the first embodiment of the present invention.

A control procedure of the data processing/display device 5 in the present embodiment will next be described. FIG. 7 is a flowchart showing the contents of control of the data processing/display device 5 in the present embodiment.

Figure 8:
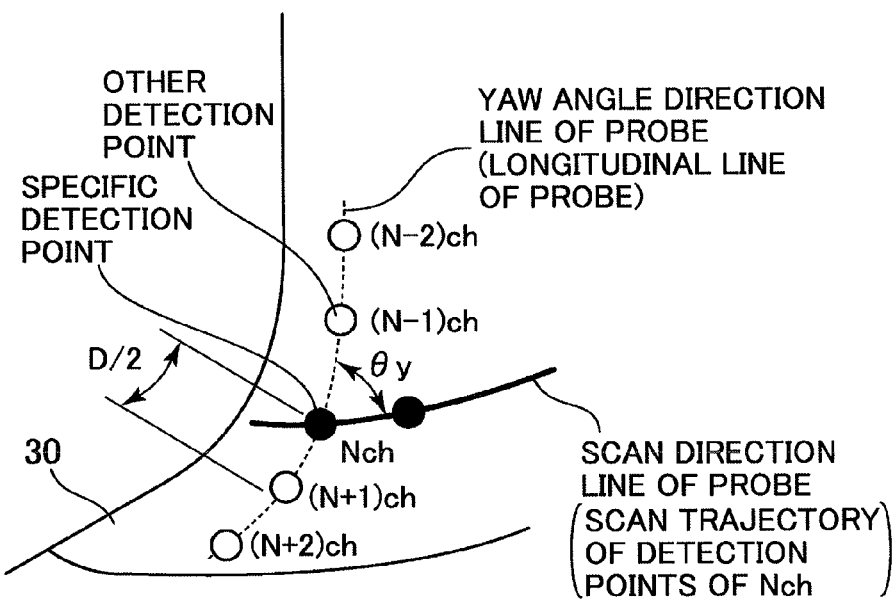
FIG. 8 is a diagram for describing a method of acquiring three-dimensional coordinates of detection points in the first embodiment of the present invention.

In FIG. 7, at step 201, the detection point three-dimensional coordinate acquisition unit 25 of the data processing/display device 5 first receives control parameters of the scanning device 2 related to the number of start trigger signals from the scan control device 3. Then, the detection point three-dimensional coordinate acquisition unit 25 computes a three-dimensional coordinate of the detection point O of the N channel based on the control parameters and the like of the scanning device 2 for every number of start trigger signals (in other words, for each scan position of probe 1). Thereafter, the procedure proceeds to step 202, where the detection point three-dimensional coordinate acquisition unit 25 reads the three-dimensional model 30 of the inspection surface from the three-dimensional model storage unit 24. As shown in FIG. 8, the detection point three-dimensional coordinate acquisition unit 25 plots detection points O on the three-dimensional model 30 based on the three-dimensional coordinates of the detection points O of the N channel, and creates or generates a scan trajectory (equivalent to a scan direction line of the probe 1) of the detection points O that smoothly connect those.

Thereafter, the procedure proceeds to step 203, where the detection point three-dimensional coordinate acquisition unit 25 computes a yaw angle θy of the probe 1 based on the control parameters and the like of the scanning device 2 for every number of start trigger signals (in other words, for each scan position of probe 1). Then, the procedure proceeds to step 204, where the detection point three-dimensional coordinate acquisition unit 25 creates, on the three-dimensional model 30 of the inspection surface, each yaw angle direction line (in other words, longitudinal line of probe 1) that passes through the detection point O based on the yaw angle θy of each scan position of the probe 1 as shown in FIG. 8.

Thereafter, the procedure proceeds to step 205, where the detection point three-dimensional coordinate acquisition unit 25 reads the detection point interval D/2 on the substrate 9 from the probe structure storage unit 23. As shown in FIG. 8, the detection point three-dimensional coordinate acquisition unit 25 plots detection points of other channels other than the N channel along each yaw angle direction line based on the detection point intervals D/2 on the substrate 9, and thereby computes three-dimensional coordinates of the detection points of the other channels. The three-dimensional coordinate of the detection point O of the N channel and the detection points of the other channels both obtained at steps 201 and 205 are stored in the detection point three-dimensional storage unit 26 in association with the number of the start trigger signals (in other words, each scan position of the probe 1). Incidentally, the three-dimensional coordinates of the detection points and the three-dimensional model 30 of the inspection surface are based on the same coordinate system.

Steps 201 through 205 described above may be performed before the scanning/flaw detection of the multi-coil probe 1. Alternatively, they may be performed during the scanning/flaw detection or after the scanning/flaw detection. After the scanning/flaw detection of the multi-coil probe 1, the procedure proceeds to step 206, where the three-dimensional flaw detection data generation unit 27 of the data processing/display device 5 receives the detected data recorded in the eddy current flaw detection device 4. Then, the three-dimensional flaw detection data generation unit 27 reads the three-dimensional coordinates of the detection points related to the number of the start trigger signals from the detection point three-dimensional coordinate storage unit 26, and coverts the detected data to three-dimensional flaw detection data based on the three-dimensional coordinates. That is, the three-dimensional flaw detection data generation unit 27 generates three-dimensional flaw detection data including the three-dimensional coordinates of the detection points and the results of detection thereof corresponding to them.

Figure 9:
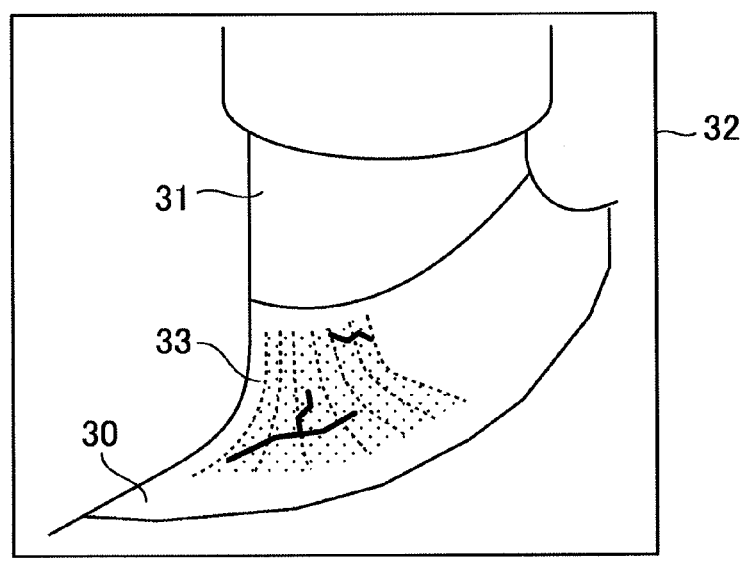
FIG. 9 is a diagram showing one example of a three-dimensional model display screen in the first embodiment of the present invention.

Thereafter, the procedure proceeds to step 207, where the display control unit 28 causes the display unit 29 to display such a three-dimensional model screen 32 as shown in FIG. 9, for example. The three-dimensional model 30 of the inspection surface and the three-dimensional model 31 of the surface of the peripheral structure both stored in the three-dimensional model storage unit 24 are displayed on the three-dimensional model screen 32. The display control unit 28 causes the screen 32 of the display unit 29 to display the levels of the results of detection of the detection points in the form of changes in color tone based on the three-dimensional flaw detection data generated by the three-dimensional flaw detection data generation unit 27, while the detection points are being associated with each other on the three-dimensional model 30 of the inspection surface (refer to a flaw-detection result display area 33 in the screen 32). Incidentally, although FIG. 9 is shown by taking for example the case where the levels of the results of detection are represented in two stages in the form of the changes in color tone, for convenience, it is needless to say that the levels may be represented in three or more stages.

Incidentally, in the present embodiment, the positions of an end of the flaw on its one side and an end thereof on its other side can be specified in the three-dimensional model screen 32. The display control unit 28 has the function of computing three-dimensional coordinates of the end on one side of the specified flaw and the end on its other side and displaying the same on the screen 32. The display control unit 28 also has the function of computing the length of the specified flaw ranging from the end on one side to the end on its other side along the shape of the flaw and displaying the same on the screen 32. Thus, the evaluation of the position, length and the like of the flaw is facilitated.

Figure 10:
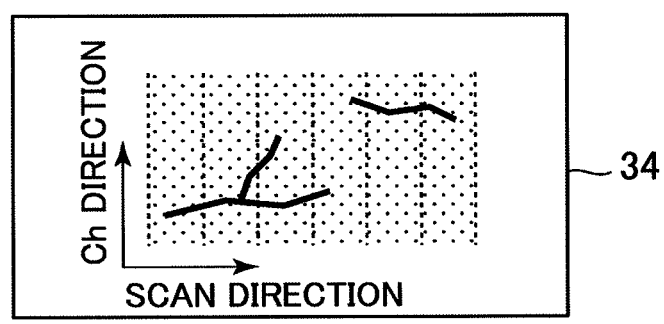
FIG. 10 is a diagram illustrating a display screen according to a comparative example.

In the present embodiment configured as described above, the data processing/display device 5 acquires the three-dimensional coordinates of the detection points corresponding to the combinations (channels) of the exciting and detecting coils for each scan position of the multi-coil probe 1. Then, the data processing/display device 5 generates the three-dimensional flaw detection data including the three-dimensional coordinates of the detection points and the results of detection corresponding to them. The data processing/display device 5 displays the three-dimensional model 30 of the inspection surface and represents in color tones, the detected results of detection points on the three-dimensional model 30 of the inspection surface, based on the three-dimensional flaw detection data. Thus, it is possible to enhance the accuracy of display of a flaw detection result without causing distortion as compared with the case where like a screen 34 shown in FIG. 10, for example, a scan area is represented by a two-dimensional coordinate system with each probe scan position and each channel position on the substrate being taken as coordinates and the results of detection of respective channels are represented in color tones of pixels of their corresponding coordinates. As a result, it is possible to enhance the accuracy of evaluation of the position, length and the like of the flaw.

In the foregoing description, the detection point three-dimensional coordinate acquisition unit 25 constitutes detection point three-dimensional coordinate acquiring means, stated in Claims, which acquires three-dimensional coordinates of detection points for each scan position of an eddy current flaw detection probe. The three-dimensional flaw detection data generation unit 27 constitutes three-dimensional flaw detection data generating means which generates three-dimensional flaw detection data including the three-dimensional coordinates of the detection points and detection results thereof corresponding to the three-dimensional coordinates. The display unit 29 constitutes display means which displays a three-dimensional model of a inspection surface and displays the detection results of the detection points on the three-dimensional model of the inspection surface in color tones, based on the three-dimensional flaw detection data.

The probe structure storage unit 23 constitutes probe structure storing means which stores in advance relations in position between the detection points on a substrate of the eddy current flaw detection probe. The step 201 performed by the detection point three-dimensional coordinate acquisition unit 25 constitutes first detection point three-dimensional coordinate computing means which computes a three-dimensional coordinate of a specific detection point of the detection points corresponding to the scan position of the eddy current flaw detection probe based on control parameters of a scanning device. The step 203 performed by the detection point three-dimensional coordinate acquisition unit 25 constitutes probe attitude angle computing means which computes a yaw angle of the eddy current flaw detection probe based on the control parameters of the scanning device. The steps 202, 204 and 205 performed by the detection point three-dimensional coordinate acquisition unit 25 constitute second detection point three-dimensional coordinate computing means which plots the specific detection point on the three-dimensional model of the inspection surface, plots other detection points than the specific detection point on the three-dimensional model of the inspection surface based on the yaw angle of the eddy current flaw detection probe and the relations in position between the detection points on the substrate, and thereby computes three-dimensional coordinates of said other detection points.

Figure 11:
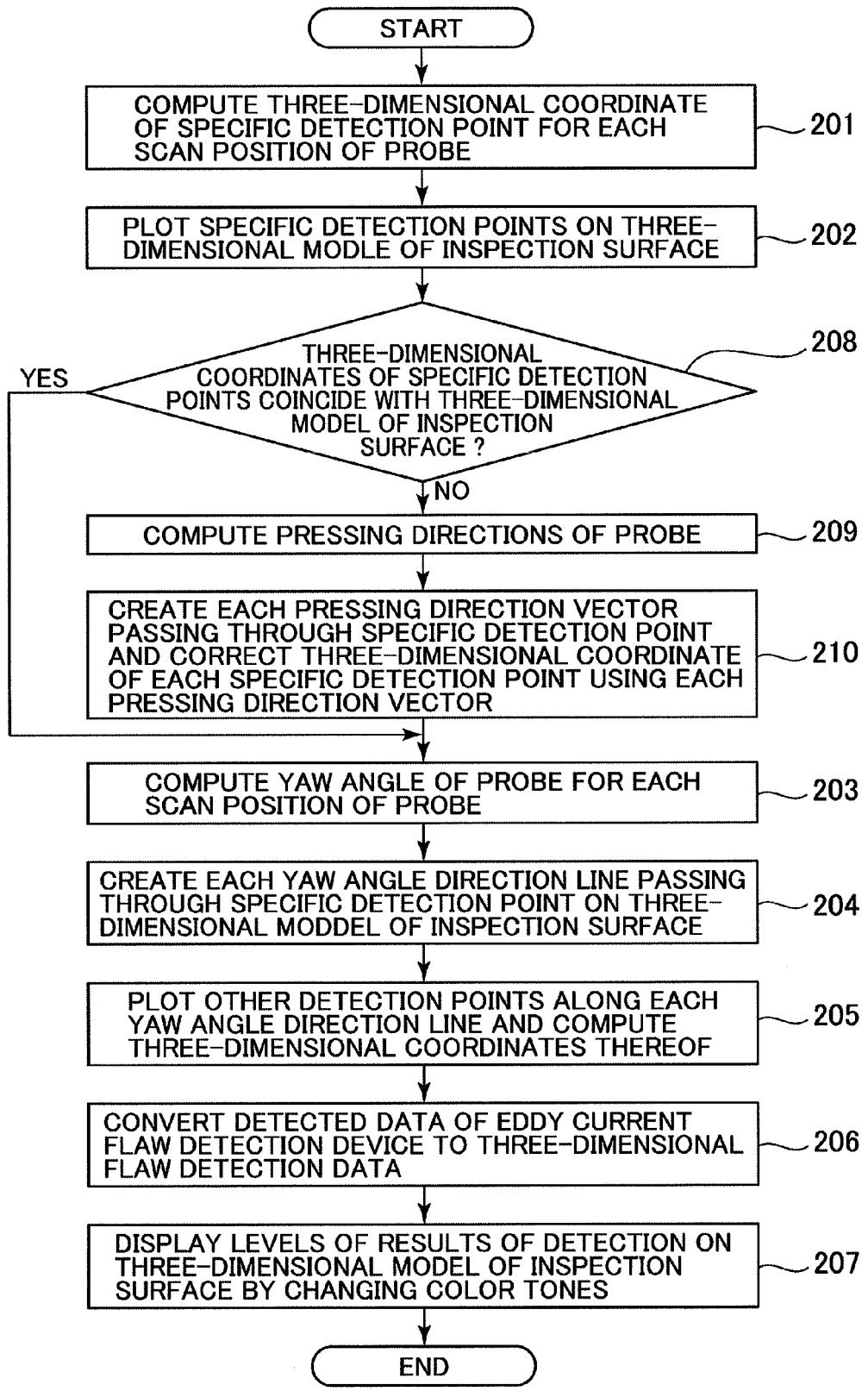
FIG. 11 is a flowchart showing the contents of control of a data processing/display device in a first modification of the present invention.

Incidentally, although not explained in particular in the first embodiment, there is a possibility that the three-dimensional coordinates of the detection points O of the N channel computed at step 202 of FIG. 7 will not coincides with the three-dimensional model 30 of the inspection surface due to, for example, reasons such as data rounding errors at the three-dimensional model 30 of the inspection surface. Therefore, the data processing/display device 5 may perform such control as shown in FIG. 11. FIG. 11 is a flowchart showing the contents of control of a data processing/display device 5 in a first modification. Incidentally, parts identical to those in the first embodiment are denoted by the same reference numerals, and their description will be omitted as appropriate.

Figure 12:
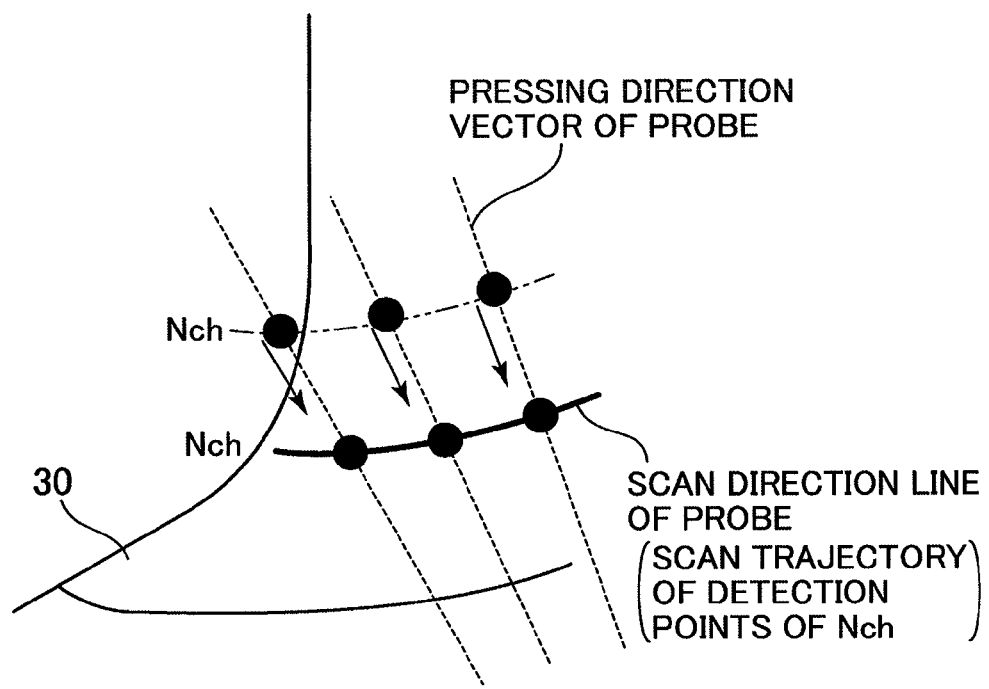
FIG. 12 is a diagram for describing a method of correcting a three-dimensional coordinate of a specific detection point in the first modification of the present invention.

In the present modification, at step 208, a detection point three-dimensional coordinate acquisition unit 25 of the data processing/display device 5 determines whether the three-dimensional coordinates of the detection points O of the N channel computed at step 201 coincide with the three-dimensional model 30 of the inspection surface. For example, when the three-dimensional coordinates of the detection points O of the N channel coincide with the three-dimensional model of the inspection surface, the determination of step 208 is satisfied, and the procedure proceeds to step 203. On the other hand, when the three-dimensional coordinates of the detection points O of the N channel do not coincide with the three-dimensional model of the inspection surface, the determination of step 208 is not satisfied, and the procedure proceeds to step 209. At step 209, the detection point three-dimensional coordinate acquisition unit 25 computes the direction (refer to FIGS. 4A and 4B) of pressing by the probe 1 based on the control parameters of the scanning device 2 for every number of start trigger signals (in other words, for each scan position of probe 1). Thereafter, the procedure proceeds to step 210, where the detection point three-dimensional coordinate acquisition unit 25 creates pressing direction vectors passing through the detection points O of the N channel respectively as shown in FIG. 12 and computes correction values for the three-dimensional coordinates of the detection points O of the N channel by intersection points of both the pressing direction vectors and the three-dimensional model 30 of the inspection surface. Even in such a modification, advantages similar to those in the first embodiment can be obtained.

In the foregoing description, The step 209 performed by the detection point three-dimensional coordinate acquisition unit 25 constitutes probe pressing direction computing means, stated in Claims, which computes a direction for pressing the eddy current flaw detection probe against the inspection surface based on the control parameters of the scanning device. The step 210 performed by the detection point three-dimensional coordinate acquisition unit 25 constitutes that, when the computed three-dimensional coordinate of the specific detection point does not coincide with the three-dimensional model of the inspection surface, the first detection point three-dimensional coordinate computing means moves the three-dimensional coordinate of the specific detection point in the pressing direction to correct the three-dimensional coordinate so as to coincide with the three-dimensional model of the inspection surface.

Although the first embodiment and the first modification have explained for example the case where the data processing/display device 5 performs step 201 (computation of the three-dimensional coordinates of the detection points O of the N channel) and step 203 (computation of the yaw angles θy of the probe 1) in FIGS. 7 and 11, the scan control device 4 may perform these steps instead of the data processing/display device 5. Although the first modification has explained for example the case where the data processing/display device 5 performs step 209 (computation of the pressing directions of the probe 1) of FIG. 11, the scan control device 4 may perform step 209 instead of the data processing/display device 5. Although the first embodiment and so forth have explained for example the case where the eddy current flaw detection device 4 and the data processing/display device 5 are configured as separate components, the eddy current flaw detection device and the data processing/display device may alternatively be configured as integral, for example. Even in these cases, advantages similar to the above can be obtained.

A second embodiment of the present invention will be explained with reference to FIGS. 13 through 17. Components similar to those in the first embodiment are denoted by the same reference numerals, and their description will be omitted as appropriate.

Figure 13:
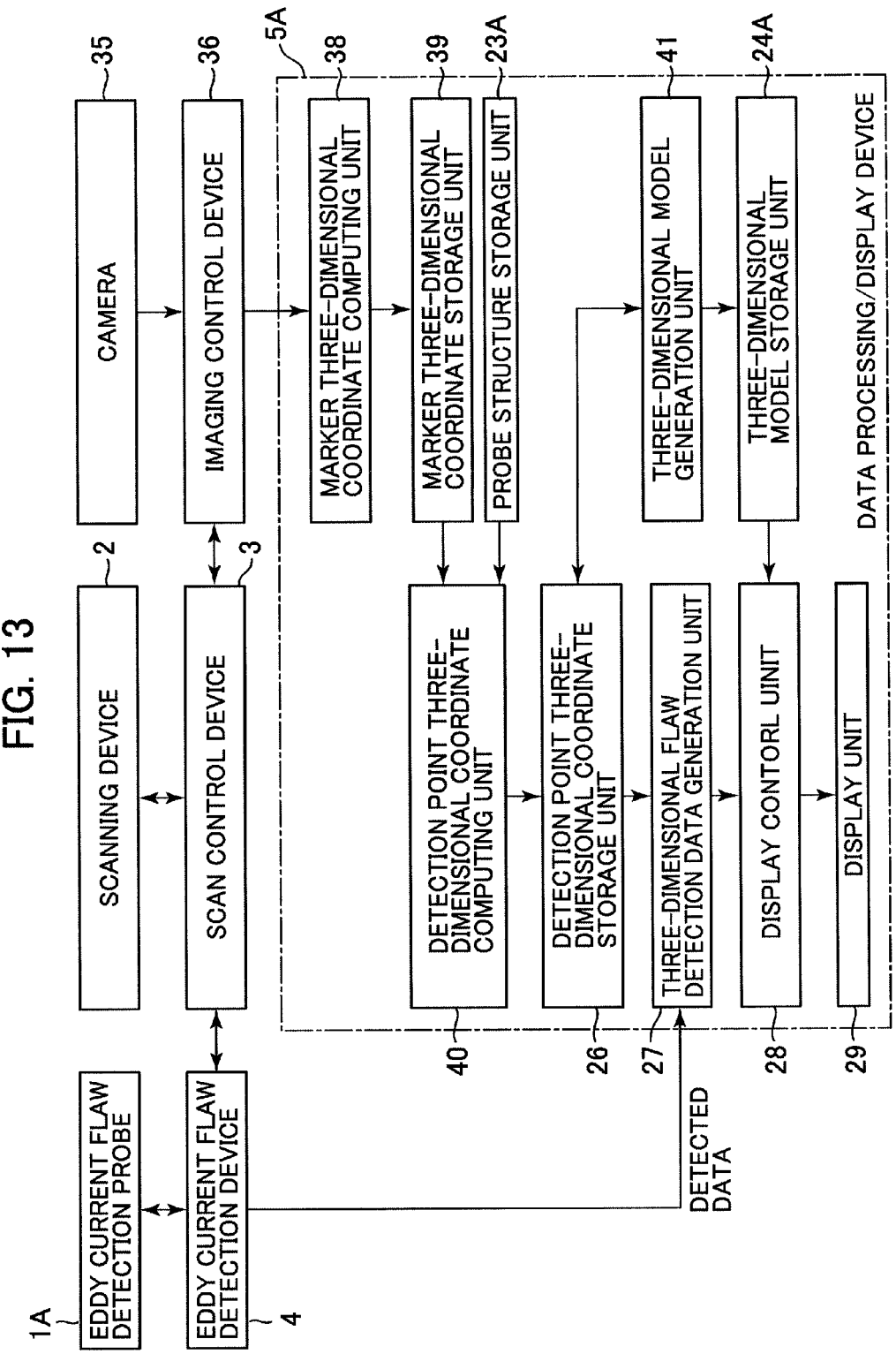
FIG. 13 is a block diagram showing a configuration of an eddy current flaw detection system according to a second embodiment of the present invention.
Figure 14:
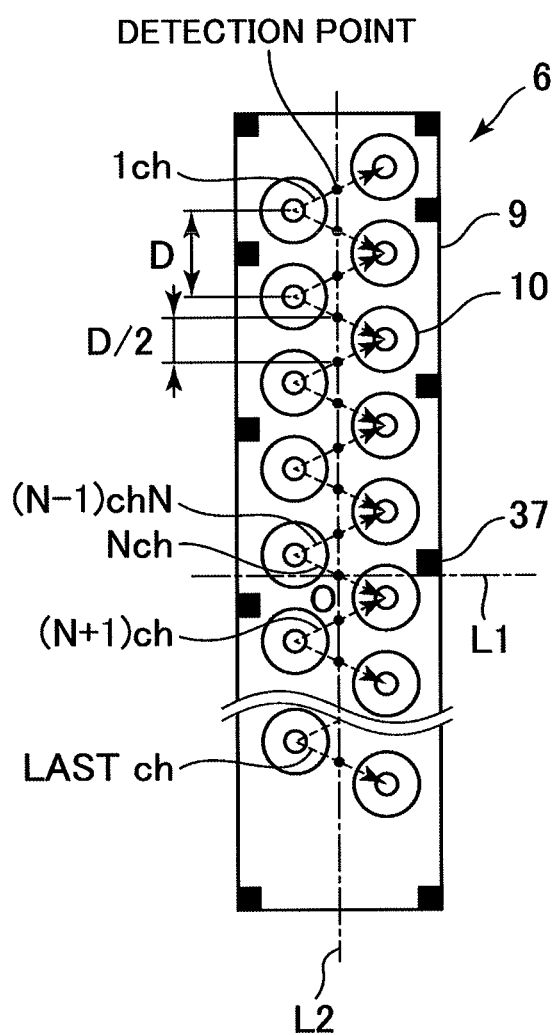
FIG. 14 is a plan view illustrating a structure of a sensor part of an eddy current flaw detection probe in the second embodiment of the present invention.
Figure 15:
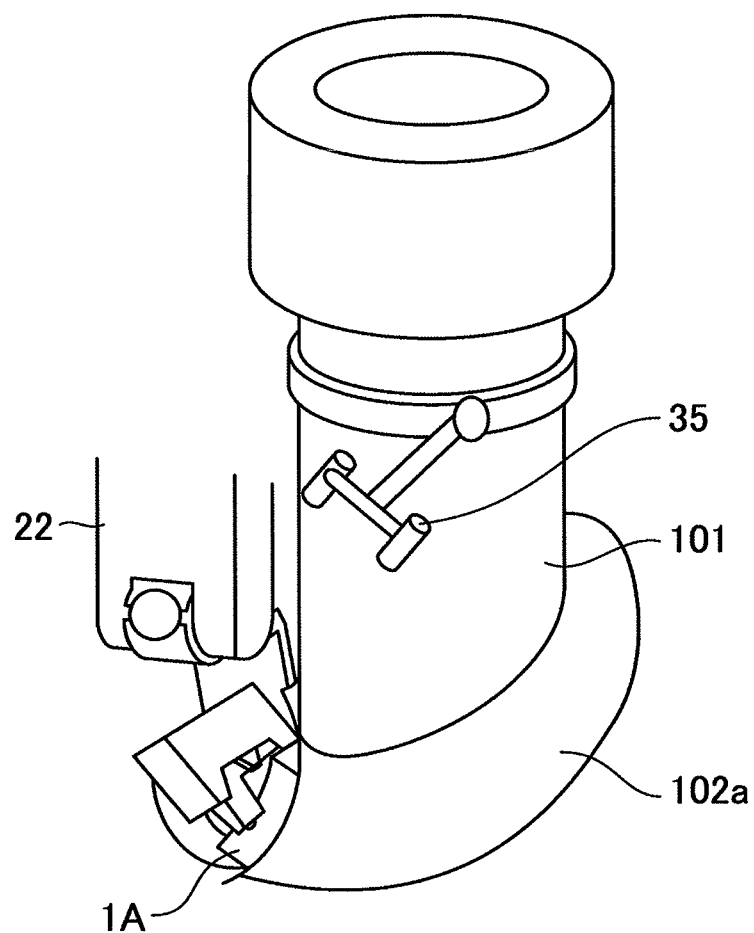
FIG. 15 is a perspective view for describing an installed position of a camera in the second embodiment of the present invention.

FIG. 13 is a block diagram showing a configuration of an eddy current flaw detection system according to the present embodiment. FIG. 14 is a plan view showing a structure of a sensor part of an eddy current flaw detection probe in the present embodiment. FIG. 15 is a perspective view for describing an installed position of a camera in the present embodiment.

The eddy current flaw detection system according to the present embodiment is equipped with an eddy current flaw detection probe (hereinafter called a multi-coil probe) 1A disposed on an inspective surface 102a, a scanning device 2 which scans the multi-coil probe 1A on the inspection surface 102a, a scan control device 3 which drives and controls the scanning device 2 to control a scan position and an attitude angle of the multi-coil probe 1A, an eddy current flaw detection device 4 which performs flaw detection control of the multi-coil probe 1A, a plurality of cameras 35 fixed to, for example, a stub tube 101 of a control rod drive or the like, an imaging control device 36 which performs imaging control of these cameras 35, and a data processing/display device 5A which processes data received from the imaging control device 36 and the eddy current flaw detection device 4 to display a result of flaw detection.

The sensor part 6 of the multi-coil probe 1A is provided with a plurality of markers 37 fixed to an outer edge portion on the upper surface side (side opposite to the inspection surface 102a) of a substrate 9. These markers 37 are provided so as to be exposed from a sponge 11 and are capable of being imaged by the cameras 35.

The scan control device 3 transmits a start trigger signal to the eddy current flaw detection device 4 and the imaging control device 36 every time it drives and controls the scanning device 2 to scan the multi-coil probe 1A with a predetermined scan pitch (in other words, for each scan position of multi-coil probe 1A). The imaging control device 36 controls the cameras 35 in response to the start trigger signal outputted from the scan control device 3 to image the markers 37 and records images of the markers 37 in association with the number of the start trigger signals.

The data processing/display device 5A that is an essential part of the present embodiment has, as functional constituents, a probe structure storage unit 23A, a three-dimensional model storage unit 24A, a detection point three-dimensional coordinate storage unit 26, a three-dimensional flaw detection data generation unit 27, a display control unit 28, a display unit 29, a marker three-dimensional coordinate computing unit 38, a marker three-dimensional coordinate storage unit 39, a detection point three-dimensional coordinate computing unit 40 and a three-dimensional model generation unit 41. The probe structure storage unit 23A stores in advance, layout relations between the substrate 9 and the markers 37 at the multi-coil probe 1A and layout relations between the substrate 9 and a plurality of detection points.

Figure 16:
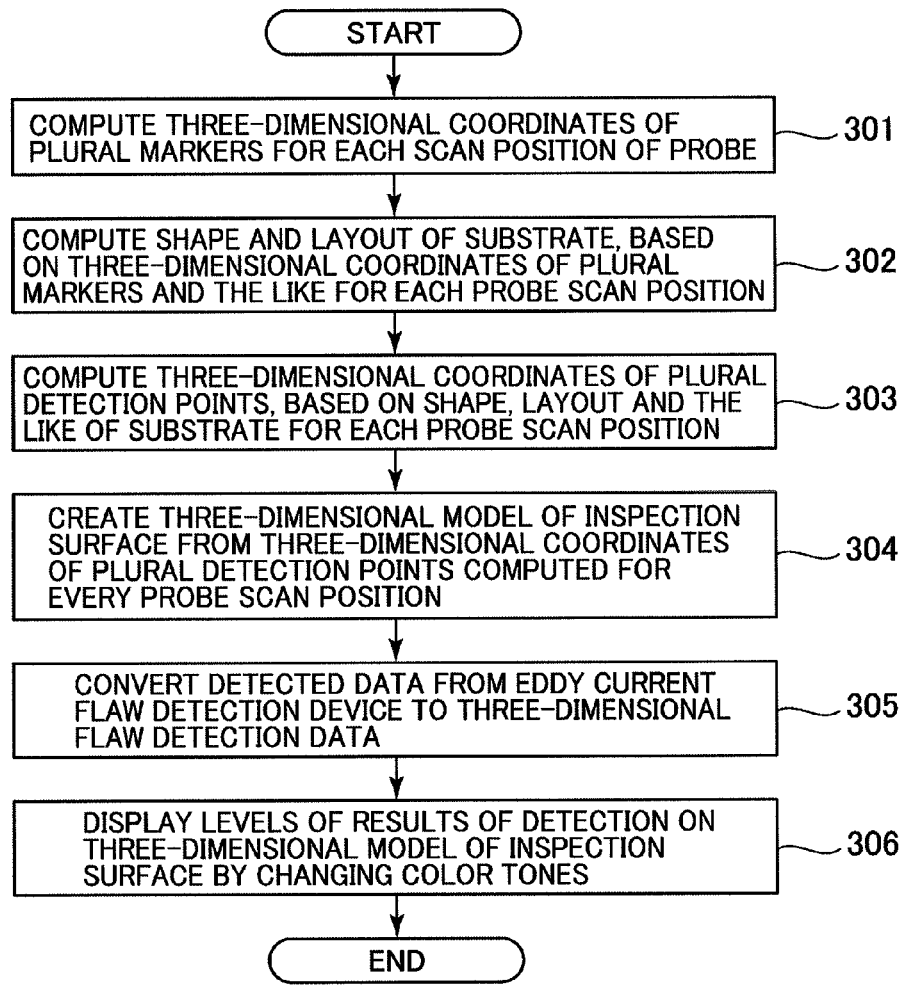
FIG. 16 is a flowchart showing the contents of control of a data processing/display device in the second embodiment of the present invention.

A control procedure of the data processing/display device 5A in the present embodiment will next be described referring FIG. 16. FIG. 16 is a flowchart showing the contents of control by the data processing/display device 5A in the present embodiment.

In FIG. 16, at step 301, the marker three-dimensional coordinate computing unit 38 of the data processing/display device 5A receives images of the markers 37 associated with the number of the start trigger signals from the imaging control device 36. Then, the marker three-dimensional coordinate computing unit 38 calculates three-dimensional coordinates of the markers 37 based on the images of the markers 37 for every number of start trigger signals (in other words, for each scan position of probe 1A). The three-dimensional coordinates of the markers 37 are stored in the marker three-dimensional coordinate storage unit 39 in association with the number (in other words, the scan position of the probe 1A) of the start trigger signals.

Thereafter, the procedure proceeds to step 302, where the detection point three-dimensional coordinate computing unit 40 reads the three-dimensional coordinates of the markers 37 associated with the number of the start trigger signals from the marker three-dimensional coordinate storage unit 39. The detection point three-dimensional coordinate computing unit 40 reads the layout relations between the substrate 9 and the markers 37 from the probe structure storage unit 23A. Then, the detection point three-dimensional coordinate computing unit 40 computes the shape and layout of the substrate 9 of the multi-coil probe 1A, based on the three-dimensional coordinates of the markers and the layout relations between the substrate 9 and the markers 37 for every number of start trigger signals (in other words, for each scan position of the probe 1A).

Thereafter, the procedure proceeds to step 303, where the detection point three-dimensional coordinate computing unit 40 reads the layout relations between the substrate 9 and the detection points from the probe structure storage unit 23A. Then, the detection point three-dimensional coordinate computing unit 40 computes three-dimensional coordinates of the detection points based on the shape and layout of the substrate 9 of the multi-coil probe 1A computed at step 302, and the layout relations between the substrate 9 and the detection points for every number of start trigger signals (in other words, for each scan position of probe 1A) (refer to FIG. 17). The three-dimensional coordinates of the detection points are stored in the detection point three-dimensional coordinate storage unit 26 in association with the number (in other words, the scan position of the probe 1A) of the start trigger signals. Incidentally, the three-dimensional coordinates of the markers 37, the three-dimensional coordinates of the detection points, and a three-dimensional model 30A of the inspection surface are based on the same coordinate system.

Figure 17:
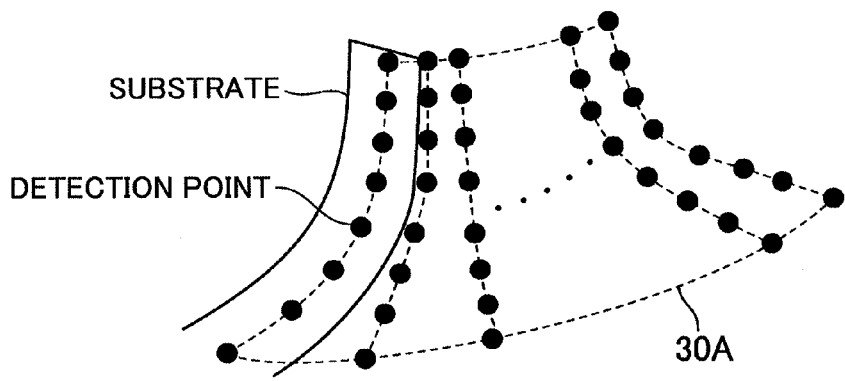
FIG. 17 is a diagram for describing a method of acquiring three-dimensional coordinates of detection points in the second embodiment of the present invention.

Thereafter, the procedure proceeds to step 304, where the three-dimensional model generation unit 41 reads the three-dimensional coordinates of the detection points from the detection point three-dimensional storage unit 26 and creates the three-dimensional model 30A of the inspection surface based on the read three-dimensional coordinates (refer to FIG. 17). The three-dimensional model 30A of the inspection surface is stored in the three-dimensional model storage unit 24A. Incidentally, the three-dimensional model generation unit 41 may read the three-dimensional coordinates of the markers 37 from the marker three-dimensional storage unit 39 and create the three-dimensional model of the inspection surface based on the read three-dimensional coordinates.

Steps 301 through 304 described above may be performed during the scanning of the multi-coil probe 1A at a preparation stage or after its scanning. Alternatively, they may be performed during the scanning/flaw detection of the multi-coil probe 1A at an inspection stage or after its scanning/flaw detection. Then, after the scanning/flaw detection of the multi-coil probe 1A, the procedure proceeds to step 305, where the three-dimensional flaw detection data generation unit 27 of the data processing/display device 5A receives the detected data recorded in the eddy current flaw detection device 4. The three-dimensional flaw detection data generation unit 27 reads the three-dimensional coordinates of the detection points associated with the number of the start trigger signals from the detection point three-dimensional coordinate storage unit 26, and converts the detected data to their corresponding three-dimensional flaw detection data, based on the read three-dimensional coordinates. That is, the three-dimensional flaw detection data generation unit 27 generates the three-dimensional flaw detection data including the three-dimensional coordinates of the detection points and detection results thereof corresponding to those.

Thereafter, the procedure proceeds to step 306, where the display control unit 28 causes the display unit 29 to display a three-dimensional model screen. The three-dimensional model 30A of the inspection surface stored in the three-dimensional model storage unit 24A is displayed on the three-dimensional model screen. Based on the three-dimensional flaw detection data generated by the three-dimensional flaw detection data generation unit 27, the levels of the results of detection of the detection points are displayed in the form of changes in color tone while the detection points are being brought into correspondence on the three-dimensional model 30A of the inspection surface.

Even in the present embodiment configured as described above, the accuracy of display of a flaw detection result can be enhanced without causing distortion as with the first embodiment. As a result, it is possible to enhance the evaluation accuracy of the position, length and the like of a flaw.

In the foregoing description, the cameras 35 constitute imaging means, stated in Claims, which images markers for each scan position of an eddy current flaw detection probe. The probe structure storage unit 23A constitutes probe structure storing means which stores in advance layout relations between a substrate and the markers at the eddy current flaw detection probe and layout relations between the substrate and detection points.

The marker three-dimensional coordinate computing unit 38 constitutes marker three-dimensional coordinate computing means which computes three-dimensional coordinates of the markers based on images of the markers for each scan position of the eddy current flaw detection probe. The detection point three-dimensional coordinate computing unit 40 constitutes detection point three-dimensional coordinate computing means which computes a shape and layout of the substrate based on the three-dimensional coordinates of the markers and the layout relations between the substrate and the markers for each scan position of the eddy current flaw detection probe, and further computes three-dimensional coordinates of the detection points based on the layout relations between the substrate and the detection points. These marker three-dimensional coordinate computing unit 38 and detection point three-dimensional coordinate computing unit 40 constitute detection point three-dimensional coordinate acquiring means which acquires three-dimensional coordinates of the detection points for each scan position of the eddy current flaw detection probe. The three-dimensional flaw detection data generation unit 27 constitutes three-dimensional flaw detection data generating means which generates three-dimensional flaw detection data including the three-dimensional coordinates of the detection points and detection results thereof corresponding to the three-dimensional coordinates.

The three-dimensional model generation unit 41 constitutes three-dimensional model generating means which generates a three-dimensional model of a inspection surface based on the three-dimensional coordinates of the detection points or the three-dimensional coordinates of the markers which have been computed for each scan position of the eddy current flaw detection probe. The display unit 29 constitutes not only display means displays the three-dimensional model of the inspection surface generated by the three-dimensional model generating means, but also display means which displays the three-dimensional model of the inspection surface and displays the detection results of the detection points on the three-dimensional model of the inspection surface in color tones, based on the three-dimensional flaw detection data.

Incidentally, although the second embodiment has explained for example the case where the data processing/display device 5A creates and displays the three-dimensional model 30A of the inspection surface, the present embodiment is not limited to it. As with the first embodiment, a three-dimensional model 30 of an inspection surface and a three-dimensional model 31 of a surface of a peripheral structure both of which have been prepared in advance, may be displayed. Even in this case, advantages similar to the above can be obtained.

Figure 18:
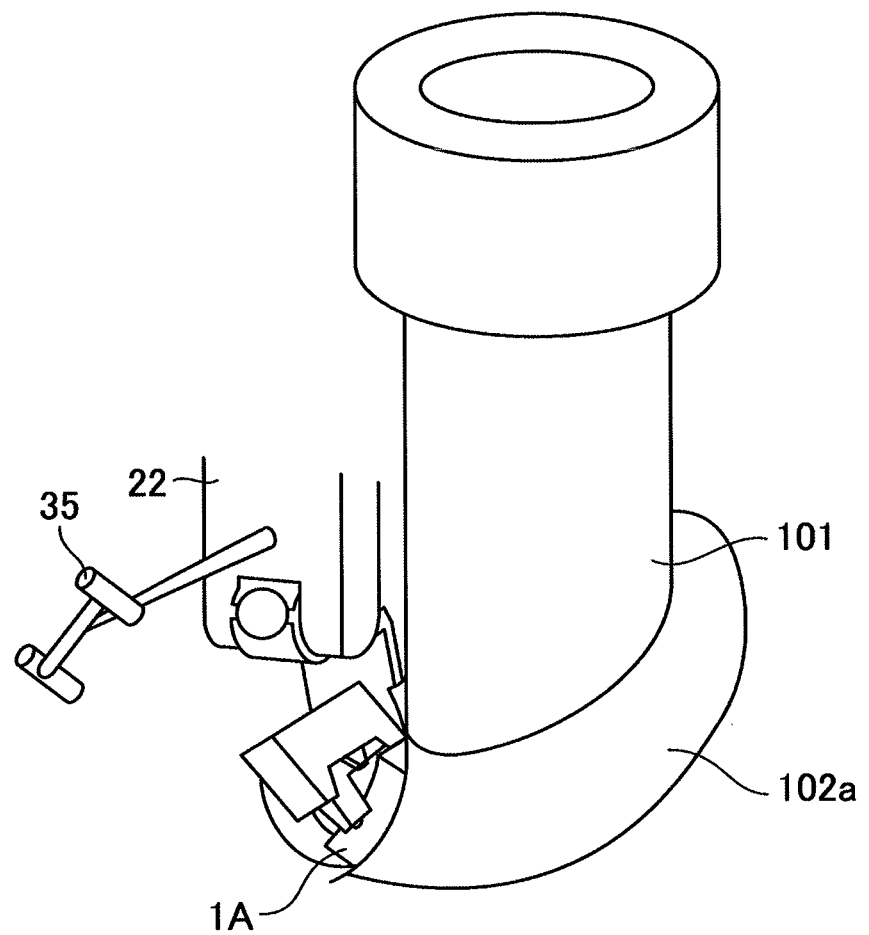
FIG. 18 is a perspective view for describing an installed position of a camera in a second modification of the present invention.

Although the second embodiment has explained for example the case where the cameras 35 are fixed to the stub tube 101 of the control rod drive or the like and not moved along with the multi-coil probe 1A, the present embodiment is not limited to it. As shown in FIG. 18, for example, they may be fixed to a manipulator 22 and moved along with the multi-coil probe 1A. In such a modification, a marker three-dimensional coordinate computing unit 38 of the data processing/display device 5A receives control parameters of the scanning device 2 associated with the number of the start trigger signals from the scan control device 3. The marker three-dimensional coordinate computing unit 38 computes the layout and attitude of each camera 35 based on the control parameters of the scanning device 2 for each number of start trigger signals (in other words, for each scan position of probe 1A). The marker three-dimensional coordinate computing unit 38 may compute the three-dimensional coordinates of the markers 37 based on the images of the markers 37 and the layouts and attitudes of the cameras 35 for every number of the start trigger signals (in other words, for each scan position of the probe 1A). Even in the present modification, advantages similar to those in the second embodiment can be obtained.

Figure 19:
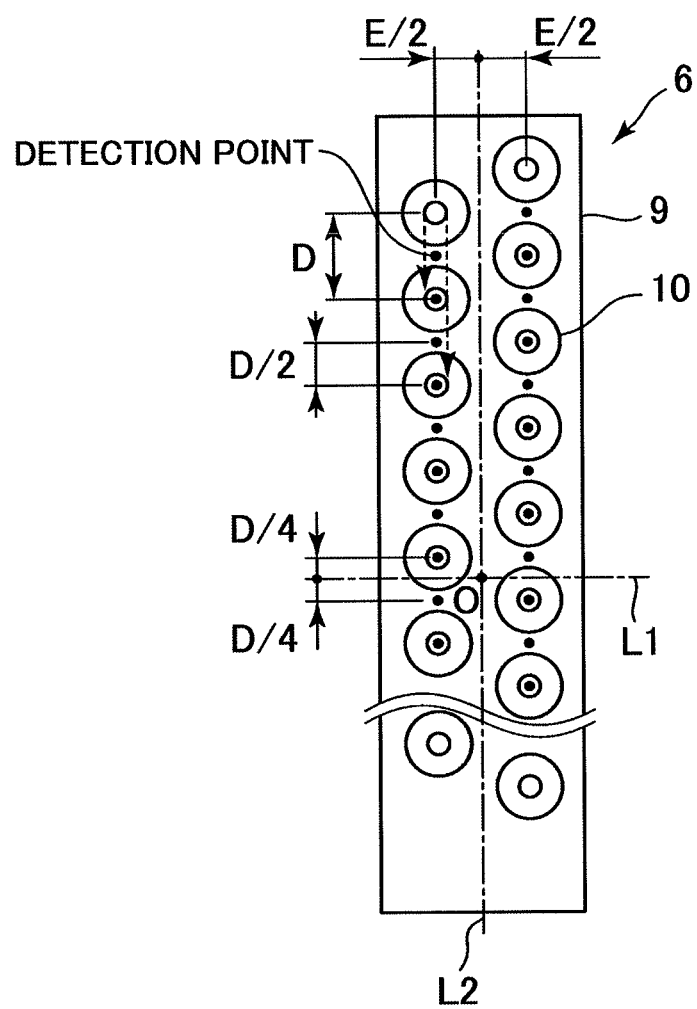
FIG. 19 is a diagram showing combined patterns of exciting and detecting coils in a third modification of the present invention.

Although each of the first and second embodiments and so forth has explained for example the case where the coils are sequentially switched to the combinations of the exciting and detecting coils placed in the layout relationship as viewed in the transverse direction of the probe as indicated by the arrows of the dotted lines in FIG. 3, they may sequentially be switched to combinations of exciting and detecting coils placed in a layout relationship as viewed in the longitudinal direction of the probe as indicated by arrows of dotted lines in FIG. 19. In such a modification, the probe structure storage unit 23 of the data processing/display device 5 (or the probe structure storage unit 23A of the data processing/display device 5A) may store in advance intervals E between coils as viewed in the transverse direction of the probe, and intervals E/2 and D/4 or the like related to a specific detection point on the substrate 9. Even in the present modification, advantages similar to the above can be obtained.

Although each of the first and second embodiments and the like has explained for example the case where the coils 10 of the eddy current flaw detection probe 1 or 1A are arranged in two rows in triangular lattice form, it is not limited to this. They may be arranged in, for example, one row or three or more rows. Alternatively, they may be arranged in quadrangular lattice form. Although each of the first and second embodiments and the like has explained for example the case where the eddy current flaw detection probe 1 or 1A has the combinations (channels) of the exciting and detecting coils in large numbers, it is not limited to this. The eddy current flaw detection probe may have at least two combinations (channels). That is, The eddy current flaw detection probe may have at least one exciting coil and at least two detecting coils spaced away from each other in the direction in which they intersect with respect to the scan direction of the probe. Even in these cases, advantages similar to the above can be obtained.

Incidentally, although the above description has been made, by way of example, of the case where the weld 102 between the reactor pressure vessel 100 and the stub tube 101 of the control rod drive is inspected, i.e., the case where The eddy current flaw detection probe 1 or 1A is scanned on the surface (inspection surface) 102a of the weld 102, the invention is not limited to it. In other words, the inspection surface has been described by taking for example the case where it is approximately in the form of the truncated conical side surface in its entirety and takes on such a complicate three-dimensional shape that its axial section is concave and its curvature changes depending on the circumferential position, but is not limited to it. That is, the inspection surface may be, for example, approximately in the form of a truncated conical side surface in its entirety and take on such a three-dimensional shape that its axial section is concave and its curvature does not change depending on the circumferential position. Alternatively, the inspection surface may be, for example, approximately in the form of a truncated conical side surface in its entirety and take on such a three-dimensional shape that it does not have a curvature at its axial section. A problem of the present invention arises in that even when scanning is performed on such an inspection surface, a portion on the one side of the sensor part 6 and a portion on the other side thereof as viewed in the direction intersecting the direction of scanning of the probe 1 or 1A are different in terms of the length of a scan trajectory. Therefore, advantages similar to the above can be obtained if the present invention is applied. When the curvature of the axial section of the above inspection surface does not change depending on the circumferential position or the inspection surface does not have the curvature at its axial section as in the case of the above inspection surface, the substrate of The eddy current flaw detection probe may be formed so as to extend along the inspection surface and may not have flexibility. Even in this case, advantages similar to the above can be obtained.

What is claimed is:
1. An eddy current flaw detection system comprising:
an eddy current flaw detection probe having a substrate facing an inspection surface, and at least one exciting coil and at least two detecting coils provided on the substrate;
a scanning device which scans the eddy current flaw detection probe on the inspection surface;
a scan control device which drives and controls the scanning device to control a scan position and an attitude angle of the eddy current flaw detection probe; and
an eddy current flaw detection device which acquires results of detection of a plurality of detection points corresponding to combinations of the exciting and detecting coils for each scan position of the eddy current flaw detection probe, wherein said eddy current flaw detection system includes:
detection point three-dimensional coordinate acquiring means which acquires three-dimensional coordinates of the detection points for each scan position of the eddy current flaw detection probe;
three-dimensional flaw detection data generating means which generates three-dimensional flaw detection data including the three-dimensional coordinates of the detection points and detection results thereof corresponding to the three-dimensional coordinates;
display means which displays a three-dimensional model of the inspection surface and displays the detection results of the detection points on the three-dimensional model of the inspection surface in color tones, based on the three-dimensional flaw detection data,
probe structure storing means which stores in advance relations in position between the detection points on the substrate of the eddy current flaw detection probe,
wherein the detection point three-dimensional coordinate acquiring means includes:
first detection point three-dimensional coordinate computing means which computes a three-dimensional coordinate of a specific detection point of the detection points corresponding to the scan position of the eddy current flaw detection probe based on control parameters of the scanning device,
probe attitude angle computing means which computes a yaw angle of the eddy current flaw detection probe based on the control parameters of the scanning device, and
second detection point three-dimensional coordinate computing means which plots the specific detection point on the three-dimensional model of the inspection surface, plots other detection points than the specific detection point on the three-dimensional model of the inspection surface based on the yaw angle of the eddy current flaw detection probe and the relations in position between the detection points on the substrate, and thereby computes three-dimensional coordinates of said other detection points.

2. The eddy current flaw detection system according to claim 1,
wherein the detection point three-dimensional coordinate acquiring means further includes probe pressing direction computing means which computes a direction for pressing the eddy current flaw detection probe against the inspection surface based on the control parameters of the scanning device, and
wherein when the computed three-dimensional coordinate of the specific detection point does not coincide with the three-dimensional model of the inspection surface, the first detection point three-dimensional coordinate computing means moves the three-dimensional coordinate of the specific detection point in the pressing direction to correct the three-dimensional coordinate so as to coincide with the three-dimensional model of the inspection surface.

3. An eddy current flaw detection system comprising:
an eddy current flaw detection probe having a substrate facing an inspection surface, and at least one exciting coil and at least two detecting coils provided on the substrate;
a scanning device which scans the eddy current flaw detection probe on the inspection surface;
a scan control device which drives and controls the scanning device to control a scan position and an attitude angle of the eddy current flaw detection probe; and
an eddy current flaw detection device which acquires results of detection of a plurality of detection points corresponding to combinations of the exciting and detecting coils for each scan position of the eddy current flaw detection probe, wherein said eddy current flaw detection system includes:
detection point three-dimensional coordinate acquiring means which acquires three-dimensional coordinates of the detection points for each scan position of the eddy current flaw detection probe;
three-dimensional flaw detection data generating means which generates three-dimensional flaw detection data including the three-dimensional coordinates of the detection points and detection results thereof corresponding to the three-dimensional coordinates;
display means which displays a three-dimensional model of the inspection surface and displays the detection results of the detection points on the three-dimensional model of the inspection surface in color tones, based on the three-dimensional flaw detection data;
a plurality of markers provided in the substrate of the eddy current flaw detection probe;
imaging means which images the markers for each scan position of the eddy current flaw detection probe; and
probe structure storing means which stores in advance layout relations between the substrate and the markers at the eddy current flaw detection probe and layout relations between the substrate and the detection points,
wherein the detection point three-dimensional coordinate acquiring means includes:
marker three-dimensional coordinate computing means which computes three-dimensional coordinates of the markers based on images of the markers for each scan position of the eddy current flaw detection probe, and
detection point three-dimensional coordinate computing means which computes a shape and layout of the substrate based on the three-dimensional coordinates of the markers and the layout relations between the substrate and the markers for each scan position of the eddy current flaw detection probe, and further computes three-dimensional coordinates of the detection points based on the layout relations between the substrate and the detection points.

4. The eddy current flaw detection system according to claim 3, further including three-dimensional model generating means which generates a three-dimensional model of the inspection surface based on the three-dimensional coordinates of the detection points or the three-dimensional coordinates of the markers which have been computed for each scan position of the eddy current flaw detection probe,
wherein the display means displays the three-dimensional model of the inspection surface generated by the three-dimensional model generating means.

5. An eddy current flaw detection method comprising the steps of:
scanning an eddy current flaw detection probe on an inspection surface, the eddy current flaw detection probe having a substrate facing the inspection surface, and at least one exciting coil and at least two detecting coils provided on the substrate; and
acquiring results of detection of a plurality of detection points corresponding to combinations of the exciting and detecting coils for each scan position of the eddy current flaw detection probe, wherein said eddy current flaw detection method includes:
a first procedure for acquiring three-dimensional coordinates of the detection points for each scan position of the eddy current flaw detection probe;
a second procedure for generating three-dimensional flaw detection data including the three-dimensional coordinates of the detection points and detection results thereof corresponding to the three-dimensional coordinates; and
a third procedure for displaying a three-dimensional model of the inspection surface and displaying the detection results of the detection points on the three-dimensional model of the inspection surface in color tones based on the three-dimensional flaw detection data, wherein the first procedure includes:
a fourth procedure for computing a three-dimensional coordinate of a specific detection point of the detection points corresponding to the scan position of the eddy current flaw detection probe based on control parameters of a scanning device for scanning the eddy current flaw detection probe;
a fifth procedure for computing a yaw angle of the eddy current flaw detection probe based on the control parameters of the scanning device; and
a sixth procedure for plotting the specific detection point on the three-dimensional model of the inspection surface, plotting other detection points than the specific detection point on the three-dimensional model of the inspection surface based on the yaw angle of the eddy current flaw detection probe and relations in position between the detection points on the substrate, and thereby computing three-dimensional coordinates of said other detection points.

6. The eddy current flaw detection method according to claim 5, wherein the first procedure further includes a seventh procedure for computing a direction for pressing the eddy current flaw detection probe against the inspection surface based on the control parameters of the scanning device,
wherein when the computed three-dimensional coordinate of the specific detection point does not coincide with the three-dimensional model of the inspection surface, the fourth procedure moves the three-dimensional coordinate of the specific detection point in the pressing direction to correct the three-dimensional coordinate so as to coincide with the three-dimensional model of the inspection surface.

7. An eddy current flaw detection method comprising the steps of:
   scanning an eddy current flaw detection probe on an inspection surface, the eddy current flaw detection probe having a substrate facing the inspection surface, and at least one exciting coil and at least two detecting coils provided on the substrate; and
   acquiring results of detection of a plurality of detection points corresponding to combinations of the exciting and detecting coils for each scan position of the eddy current flaw detection probe, wherein said eddy current flaw detection method includes:
   a first procedure for acquiring three-dimensional coordinates of the detection points for each scan position of the eddy current flaw detection probe;
   a second procedure for generating three-dimensional flaw detection data including the three-dimensional coordinates of the detection points and detection results thereof corresponding to the three-dimensional coordinates; and
   a third procedure for displaying a three-dimensional model of the inspection surface and displaying the detection results of the detection points on the three-dimensional model of the inspection surface in color tones based on the three-dimensional flaw detection data, wherein the first procedure includes:
   an eighth procedure for imaging a plurality of markers provided in the substrate of the eddy current flaw detection probe for each scan position of the eddy current flaw detection probe;
   a ninth procedure for computing three-dimensional coordinates of the markers based on images of the markers for each scan position of the eddy current flaw detection probe; and
   a tenth procedure for computing a shape and layout of the substrate based on the three-dimensional coordinates of the markers and layout relations between the substrate and the markers for each scan position of the eddy current flaw detection probe, and further computing three-dimensional coordinates of the detection points based on layout relations between the substrate and the detection points.

8. The eddy current flaw detection method according to claim 7, further including an eleventh procedure for generating a three-dimensional model of the inspection surface based on the three-dimensional coordinates of the detection points or the three-dimensional coordinates of the markers which have been computed for each scan position of the eddy current flaw detection probe,
   wherein the third procedure displays the three-dimensional model of the inspection surface generated in the eleventh procedure.

* * * * *